US010575926B2

United States Patent
Kaveh et al.

(10) Patent No.: US 10,575,926 B2
(45) Date of Patent: Mar. 3, 2020

(54) MAXILLARY EXPANDER

(71) Applicant: Craniofacial Technologies Inc., Bell Canyon, CA (US)

(72) Inventors: Cameron Kaveh, Bell Canyon, CA (US); Richard Beranek, Ottawa (CA)

(73) Assignee: Craniofacial Technologies, Inc., Bell Canyon, CA (US)

(*) Notice: Subject to any disclaimer, the term of this patent is extended or adjusted under 35 U.S.C. 154(b) by 0 days.

(21) Appl. No.: 16/115,564

(22) Filed: Aug. 29, 2018

(65) Prior Publication Data

US 2019/0159873 A1  May 30, 2019

Related U.S. Application Data

(60) Provisional application No. 62/590,363, filed on Nov. 24, 2017, provisional application No. 62/676,969, filed on May 26, 2018.

(51) Int. Cl.
*A61C 7/10* (2006.01)
*A61C 8/00* (2006.01)

(52) U.S. Cl.
CPC ............ *A61C 7/10* (2013.01); *A61C 8/0096* (2013.01)

(58) Field of Classification Search
CPC .......... A61C 7/06; A61C 7/10; A61C 8/0096; A61C 8/006; A61B 17/663; A61B 17/66; A61B 17/666; A61B 17/8071; A61B 17/6433
USPC .......................................................... 433/7
See application file for complete search history.

(56) References Cited

U.S. PATENT DOCUMENTS

| | | | |
|---|---|---|---|
| 3,866,322 A | 2/1975 | Broussard et al. | |
| 3,977,082 A * | 8/1976 | Siatkowski | A61C 7/10 433/7 |
| 4,848,368 A * | 7/1989 | Kronner | A61B 17/6475 606/57 |
| 5,564,920 A | 10/1996 | Klapper et al. | |
| 5,885,290 A * | 3/1999 | Guerrero | A61B 17/663 433/7 |
| 5,902,304 A * | 5/1999 | Walker | A61B 17/663 606/282 |
| 5,904,479 A * | 5/1999 | Staples | A61C 7/10 433/7 |
| 6,328,745 B1 * | 12/2001 | Ascherman | A61B 17/663 433/7 |
| 8,529,579 B2 * | 9/2013 | Bulloch | A61B 17/663 606/105 |

(Continued)

FOREIGN PATENT DOCUMENTS

| | | |
|---|---|---|
| DE | 601 20 845 | 1/2007 |
| KR | 10-2011-0126318 | 11/2011 |

(Continued)

OTHER PUBLICATIONS

International Search Report and Written Opinion dated Oct. 22, 2018 for PCT application No. PCT/US2018/042200.

(Continued)

*Primary Examiner* — Sean M Michalski
*Assistant Examiner* — Shannel N Wright
(74) *Attorney, Agent, or Firm* — Evan Law Group LLC

(57) ABSTRACT

An orthodontic device and method to treat maxillary deficiencies by expanding the upper palate of a patient is provided. The device and method do not require any engagement with teeth of the patient.

32 Claims, 30 Drawing Sheets

(56) References Cited

U.S. PATENT DOCUMENTS

| | | | |
|---|---|---|---|
| 8,640,710 B2 | 2/2014 | Matthews | |
| 9,351,810 B2 | 5/2016 | Moon | |
| 10,166,089 B2 | 1/2019 | Kahn et al. | |
| 2002/0156485 A1 | 10/2002 | Sellers et al. | |
| 2003/0050641 A1* | 3/2003 | Mommaerts | A61B 17/663 606/71 |
| 2003/0097137 A1 | 5/2003 | Schendel | |
| 2006/0200146 A1 | 9/2006 | Doubler et al. | |
| 2009/0130620 A1* | 5/2009 | Yazdi | A61C 7/10 433/7 |
| 2011/0143300 A1* | 6/2011 | Villaalba | A61C 7/10 433/7 |
| 2011/0230885 A1 | 9/2011 | Weiner et al. | |
| 2011/0277774 A1 | 11/2011 | Connell | |
| 2012/0277749 A1* | 11/2012 | Mootien | A61B 17/663 606/70 |
| 2013/0252195 A1* | 9/2013 | Popat | A61C 7/10 433/24 |
| 2014/0186788 A1* | 7/2014 | Sheibani Nia | A61C 7/10 433/7 |
| 2015/0056566 A1* | 2/2015 | Moon | A61C 7/10 433/7 |
| 2015/0230831 A1 | 8/2015 | Altarac et al. | |
| 2016/0270883 A1* | 9/2016 | Yousefian | A61C 7/10 |
| 2016/0270884 A1* | 9/2016 | Yousefian | A61C 7/10 |
| 2017/0281315 A1* | 10/2017 | Sotiropoulos | A61C 7/023 |
| 2018/0008376 A1* | 1/2018 | Scommegna | A61C 7/10 |
| 2018/0028282 A1 | 2/2018 | Kahn et al. | |
| 2018/0311014 A1* | 11/2018 | Yousefian | A61C 8/0096 |
| 2018/0368945 A1* | 12/2018 | Moon | A61C 7/10 |
| 2019/0159873 A1 | 5/2019 | Kaveh et al. | |

FOREIGN PATENT DOCUMENTS

| | | | |
|---|---|---|---|
| KR | 10-2018-0130375 | 12/2018 | |
| KR | 1020170066389 | 12/2018 | |
| WO | WO-2005009260 A1 * | 2/2005 | A61B 17/663 |
| WO | WO-2008011698 A2 * | 1/2008 | A61C 7/10 |
| WO | 2016/185018 | 11/2016 | |
| WO | 2019/018249 | 1/2019 | |
| WO | 2019/104255 | 5/2019 | |

OTHER PUBLICATIONS

International Search Report and Written Opinion dated May 6, 2019 for PCT application No. PCT/US2018/062403.

Moon, W., "Class III treatment by combining facemask (FM) and maxillary skeletal expander (MSE)", Seminars in Orthodontics, vol. 24, issue 1, pp. 95-107, (2018).

International Search Report and Written Opinion dated Jul. 30, 2019 for PCT application No. PCT/US2019/21707.

* cited by examiner

Figure 1B:
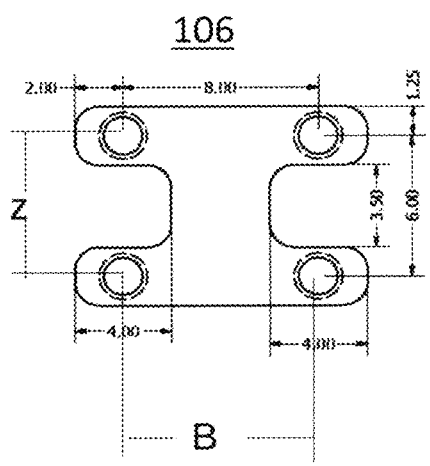
Figure 1H:
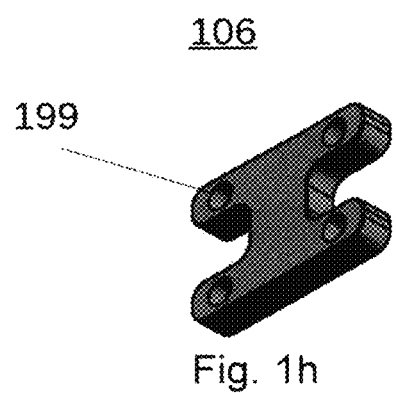
Figure 1I:
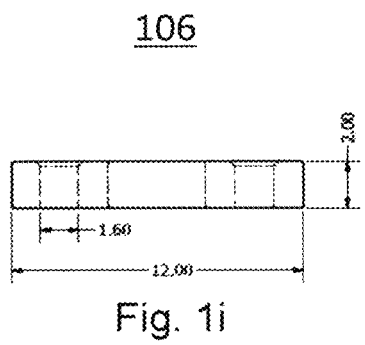
Figure 1G:
Figure 1C:
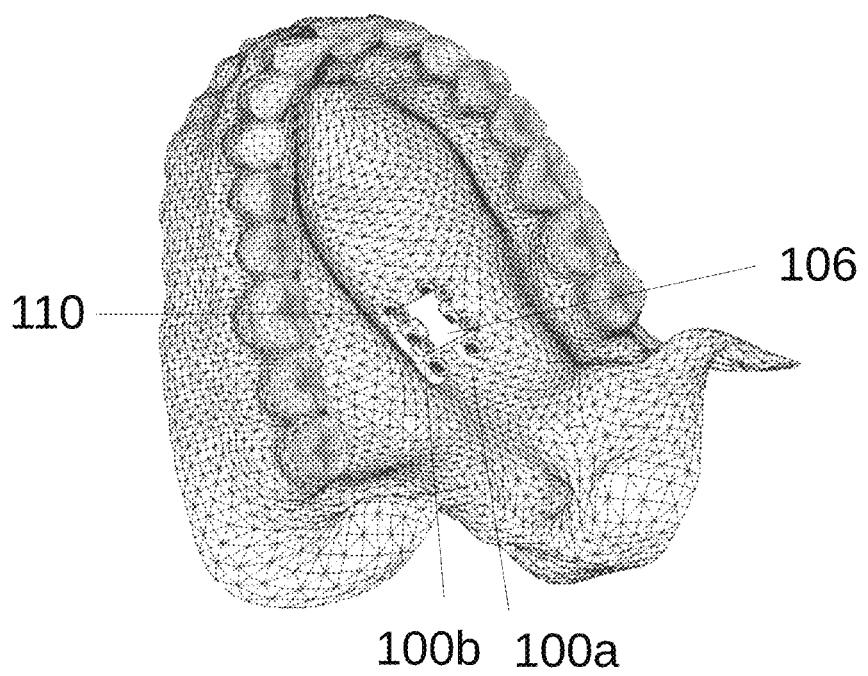
Figure 2A:
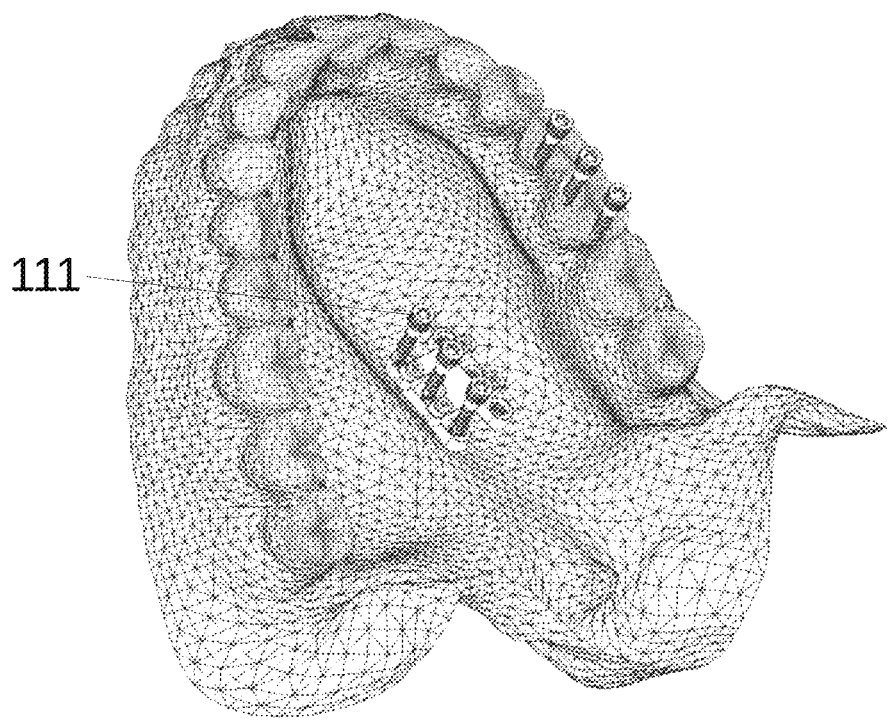
Figure 2F:
Figure 2E:
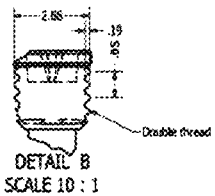
Figure 2C:
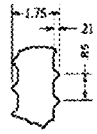
Figure 2B:
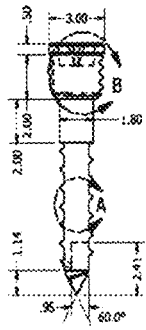
Figure 2D:

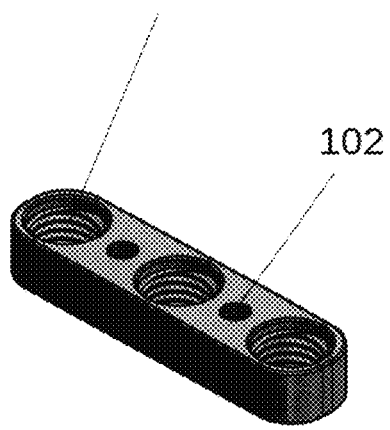
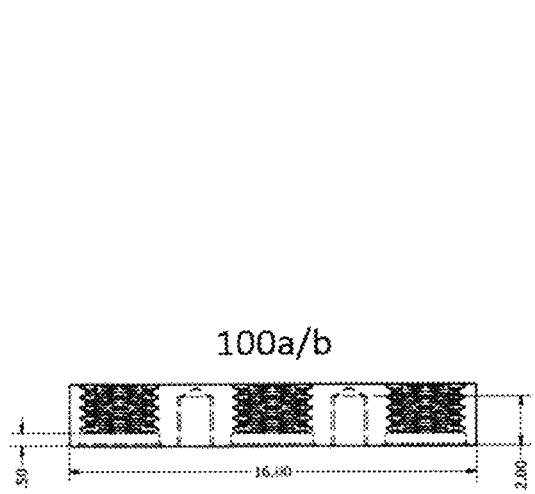
Fig. 1f
Fig. 1e
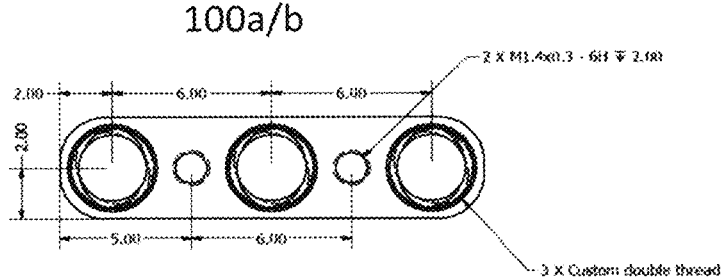
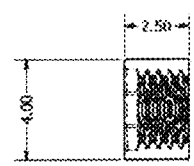
Fig. 1a
Fig. 1d

101

101

DETAIL B
SCALE 10 : 1

101

DETAIL A
SCALE 10 : 1

101

101

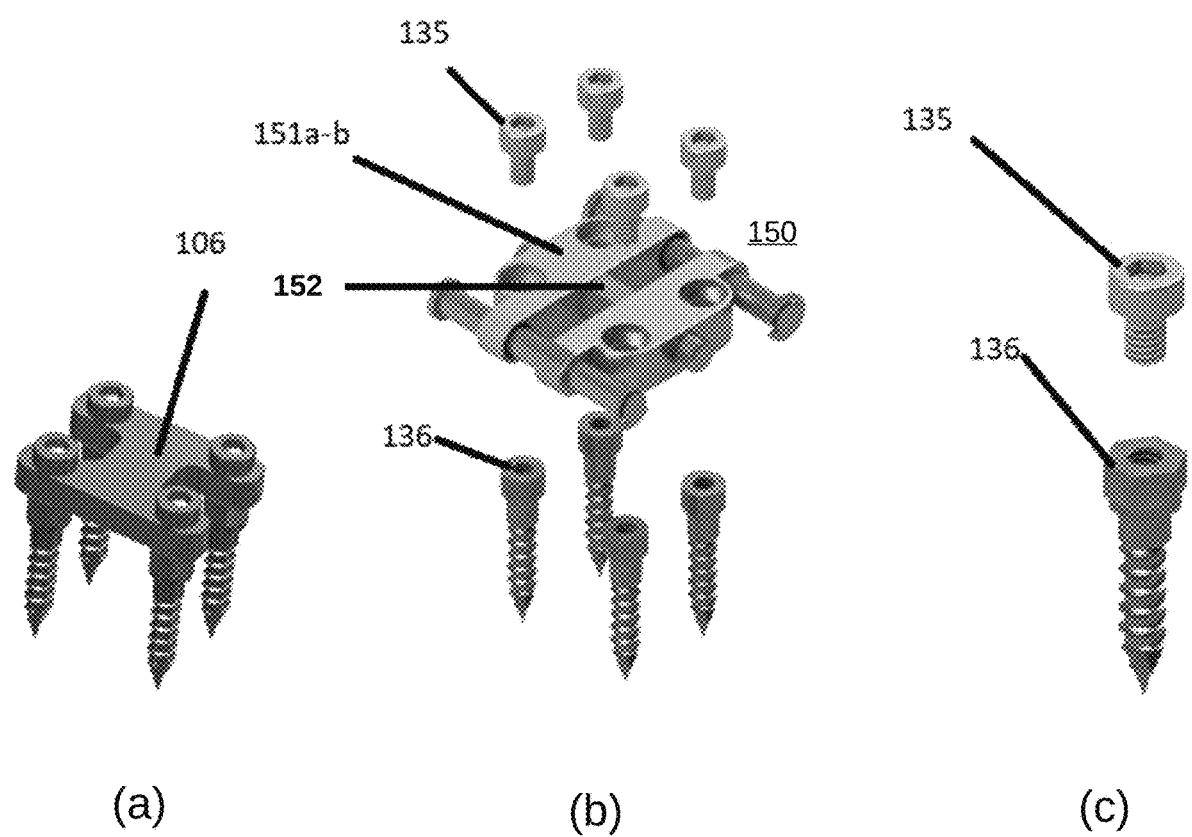
Figs. 12a-c

MAXILLARY EXPANDER

CONTINUITY INFORMATION

This application is related to and claims priority to U.S. Provisional Application filed Nov. 24, 2017 with Ser. No. 62/590,363; is related to and claims priority to U.S. Provisional Application filed May 26, 2018 with Ser. No. 62/676,969; and is related to and claims priority to U.S. Provisional Application filed Jul. 17, 2018 with Ser. No. 62/699,264; all of which are incorporated herein by reference for all purposes.

BACKGROUND

Maxillary skeletal anchorage expanders (hereafter in the background called "expander(s)") are devices used for a treatment of patients with transverse maxillary deficiency. With children, palatal expanders have been used to expand the maxillary arch to create room for the growth of permanent teeth or to widen the upper jaw so that the bottom and upper teeth will fit together better. In some cases, the jaw is expanded as a treatment to a compromised airway. Some known palatal expanders comprise and expand the maxillary arch by tooth (molar) borne anchorage means (bands) bridged together by an adjustable screw mechanism (see U.S. Pat. No. 5,564,920 Klapper). As the screw is turned, a bilateral force is generated against the teeth and jaws to cause displacement of the teeth and the maxillary arch. Once installed, the adjustable screw is rotated using a tool. The screw conventionally comprises two opposing halves, each half having a threaded portion. The force from the expanding screw is transferred through arms of the device to the banded molars and ultimately results in expansion of the maxillary dental arch and/or growth from the median palatine suture. The expander is left in for a therapeutically effective period and the patient, or patient's caregiver, activates the expander by rotating the screw a predetermined amount over a predetermined period appropriate to the expander screw configuration, age of the patient, and condition for which treatment is applied (e.g., a ¼ turn producing 0.25 mm of movement once per week; a ¼-½ turn a day producing 0.25-0.50 mm of movement a day, etc.). Following a desired expansion, a holding phase is performed, leaving the expander in place for 3-6 months for stabilization, during which time the screw is locked in place to prevent the screw from backing up. During the holding phase the tooth/jaw interface stabilizes in a new position and the palatine suture grows back together across the space, after which time the expander is removed. The expander described above expands the space across the palatine suture via forces that are directly applied to only the teeth.

Another known expander device is demonstrated in U.S. Pat. No. 9,351,810 (Moon). The Moon expander uses four mini screws/temporary anchorage devices to mount a pair of bodies to the ceiling of the hard palate on either side of palatine suture. Each of the bodies in Moon also comprise a pair of extending arms and a pair of tooth anchorage bands devices similar to that used by Klapper as mentioned above. The Moon expander comprises a double ended screw located between the pair of bodies. When the double ended screw in Moon is rotated, forces are applied directly not only to the teeth, but also by the mini screws to the hard palate on either side of the palatine suture. Unlike the Klapper device, since force is also applied directly to the hard palate, a reduced amount of force can be applied to the teeth, and a greater amount of force on the bone, which reduced force means stresses on the tooth/jaw interface can be reduced. However, the Moon expander also has a number of disadvantages. By applying forces directly to the hard palate, the mini screws are put under stress and thus are subject to potential breakage, as is also the bone structure in the area where the screws are inserted. Further, although Moon applies less force to the teeth, it nevertheless transmits force to and causes movement of the teeth, which may not be desired. For example, when treating transverse maxillary deficiency in skeletally mature individuals, transmitting force to the teeth can result in undesired alveolar effects, such as alveolar "bending," tooth root resorption, and potentially even a "scissors bite." Furthermore, Moon's expander is only supported by two mini implants on each side of the median palatine suture, which often times in more skeletally mature individuals is insufficient and inefficient at generating the desired orthopedic effects, such that could occur with surgical osteotomy followed by expansion. In these skeletally mature cases, the limit of only two mini implants on each side of the median palatine suture (4 in total) not only is inefficient at generating a desired orthopedic expansion, but also results in increased stresses on each individual mini implant and the bone around those implants. This is evidenced by the fact Moon's expander often time requires full activation of the expansion screw in skeletally mature individuals, which is 8-12 mm of activation, just to achieve opening of the median palatine suture and achieve 1-2 mm of orthopedic expansion. As a consequence of this inefficient skeletal expansion and as a consequence of the design lacking the ability to interchangeably attach different size expansion screws to the anchor bodies, in many cases when treating mature individuals, at least two of Moon's devices are required to achieve satisfactory skeletal expansion. Requiring multiple uninstallations and installations of the device causes patients to be subjected to multiple surgical procedures, increased cost, and discomfort, and requires greater effort by the clinician. Also, during the holding phase described above, the Moon expander device, as well as other known devices, requires that that it remain in a patient's mouth during the entire course of treatment. However, the expansion screw and other structures of the Moon device can disrupt tongue function and its expansion screw has a number of sharp edges, which over a long period of time can cause discomfort and potential sources of contamination.

One thing that is needed, therefore, is an expander that does not directly affect movement of teeth during expansion of the palatine suture, that enables the attachment of interchangeable expansion screws of different sizes, that reduces forces and stress applied to screws as well as the local bone supporting the screws and yet is able to more effectively distribute force along the median palatine suture, and that as well does not cause discomfort during the holding phase. Stated in another way, what is needed is an expander that can generate more substantial and efficient orthopedic effects than the prior art, while at the same time eliminating alveolar and tooth effects, and, reducing discomfort and inconvenience for the patient and clinician. Maxillary deficiency can also occur in a forward (sagittal) direction. An orthodontic device known as the Keles Facemask includes both a palatal expander and an orthodontic face bow that impart lateral and protraction forces via molar bands that are fixed to a patient's dentition. Jaw movement imparted by the Keles device causes forwardly directed downward growth of the maxilla. The Keles device relies on tooth borne forces that are then transferred to the maxilla, which is less than ideal, since movement that might otherwise be imparted to the maxilla bone is instead imparted to teeth.

Another device invented by De Clerck utilizes a bone anchor comprised of a Bollard miniplate to transfer forward protraction forces to the maxilla. The De Clerck device can be used for maxillary protraction, but it to causes rotation of the maxilla, which causes movement and growth of the maxilla to be directed not just forward, but downward, and as well requires relatively invasive mucosal surgery for installation.

What is needed is an orthodontic device that is able to impart forward movement and growth of the maxillary skeletal complex and the 9 bones that articulate with the maxilla in a manner that improves upon the prior art.

FIGURES

Referring to FIGS. 1a, 1b, 1c, 1d, 1e, 1f, 1g, 1h and 1i, there are seen representations of components of a skeletal anchorage device before being coupled intraorally to a patient's upper palate on either side of the median palatine suture.

Referring to FIGS. 2a, 2b, 2c, 2d, 2e and 2f, there are seen representations of components of a skeletal anchorage expander device during their coupling to the hard palate on either side of the median palatine suture.

Figure 3:
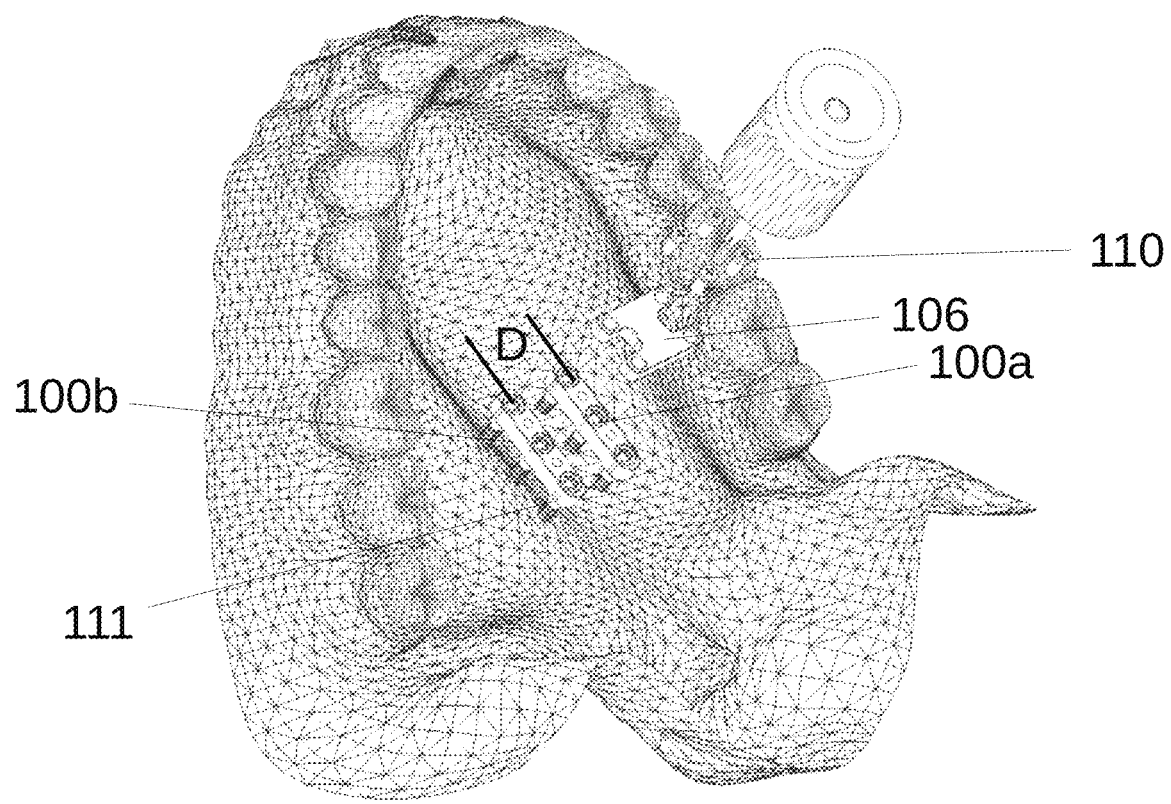

Referring to FIG. 3, there is seen a representation of components of a skeletal anchorage expander device after a pair of first bodies has been coupled to a palate of a patient and after a first fixed aligner is removed.

Referring now to FIGS. 4a-e, there are seen representations of components of a skeletal anchorage expander device that comprises an adjustable aligner and/or a pair of first bodies.

Figure 5A:
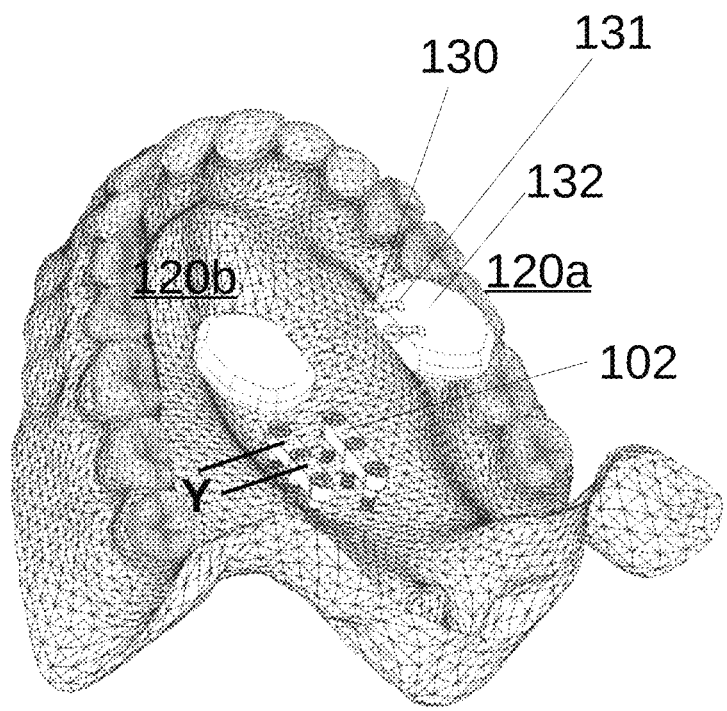

Referring to FIGS. 5a. 5b and 5c, there are seen representations of components a skeletal anchorage expander device, including of a pair of first bodies and a pair of appliances before the appliances are coupled to the pair of first bodies.

Referring to FIGS. 6a-d, there are seen representations of components of a skeletal anchorage expander device including a pair of appliances coupled to a pair of first bodies before and after an adjustable aligner is coupled to the pair of first bodies and the appliances.

Figure 7A:
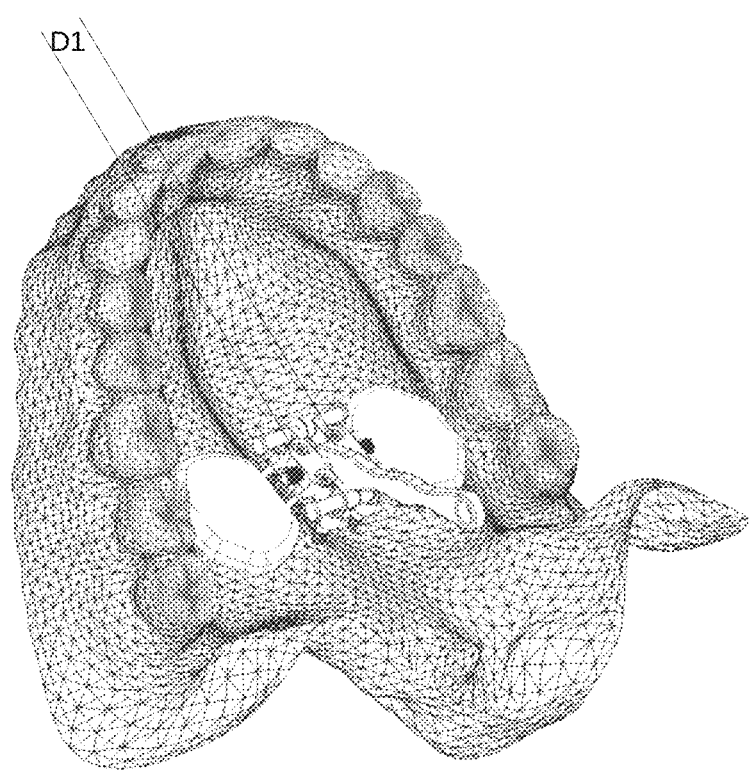
Figure 7B:
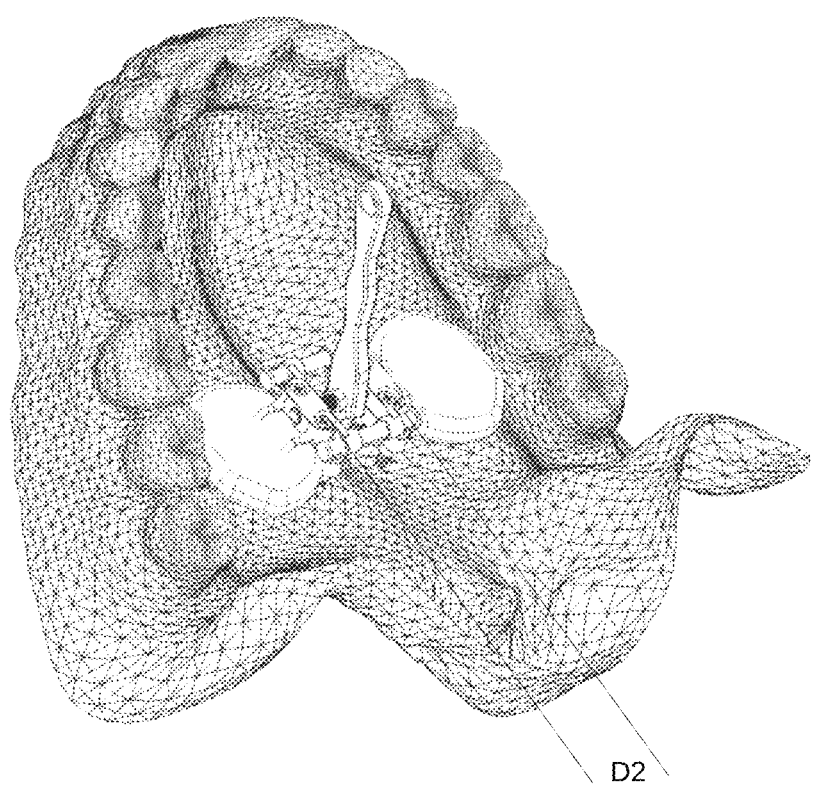

Referring to FIGS. 7a-b, there are seen representations of components of a skeletal anchorage expander device comprised of appliances before and after a distance between an adjustable aligner is increased by an adjustment mechanism.

Figure 8:
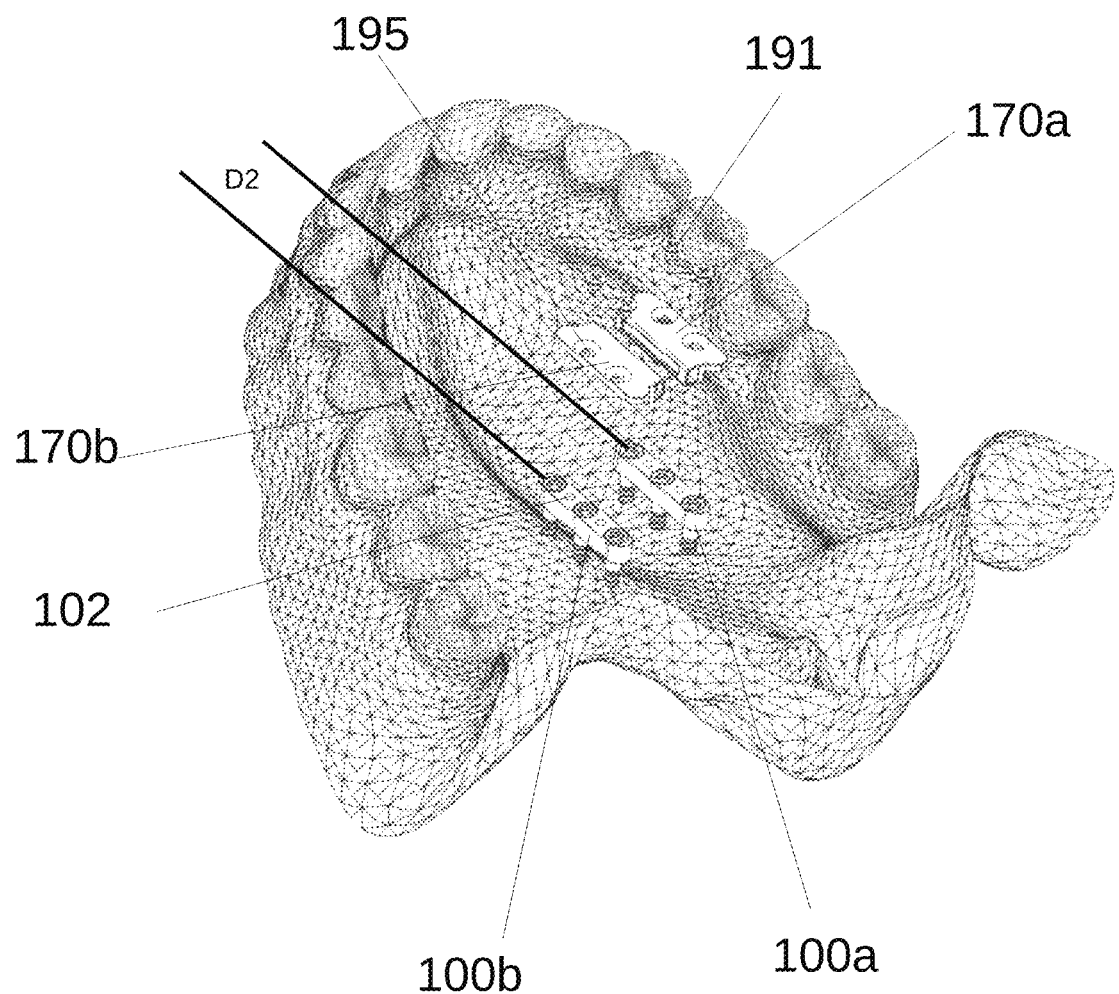

Referring to FIG. 8, there is seen a representation of a pair of first bodies after a distance between the adjustable aligner is increased by a clinically desired amount the adjustable aligner and acrylic appliances are removed.

Figure 9:
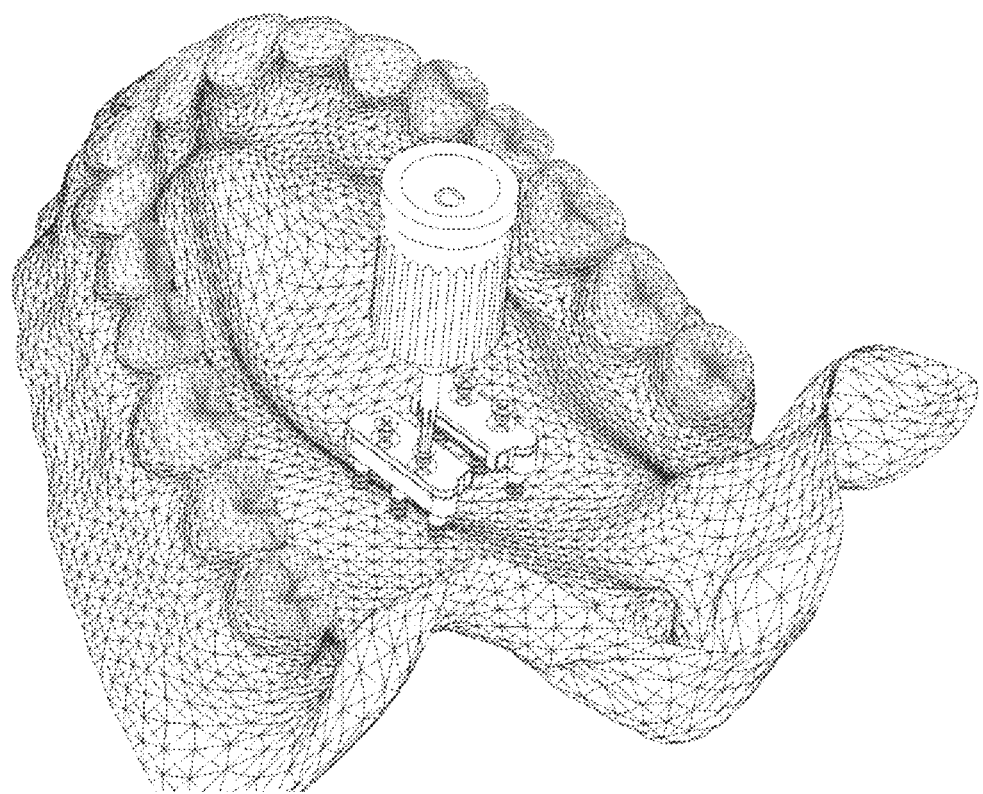
Figure 10A:
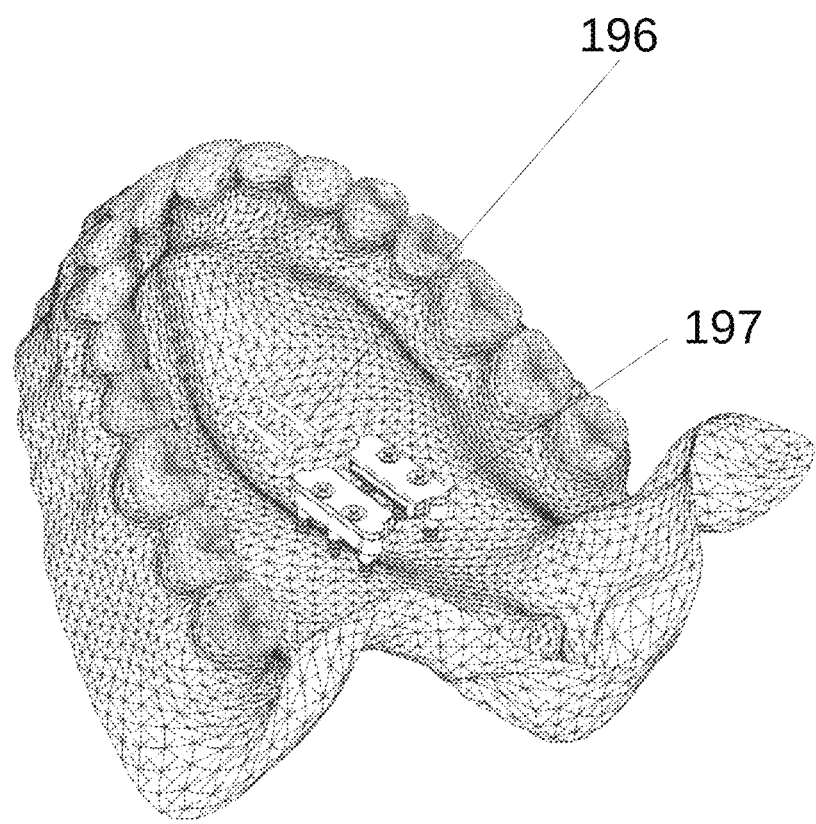
Figure 10G:
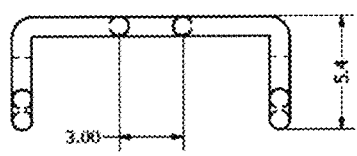
Figure 10E:
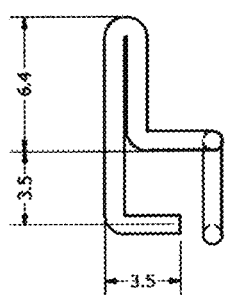
Figure 10F:
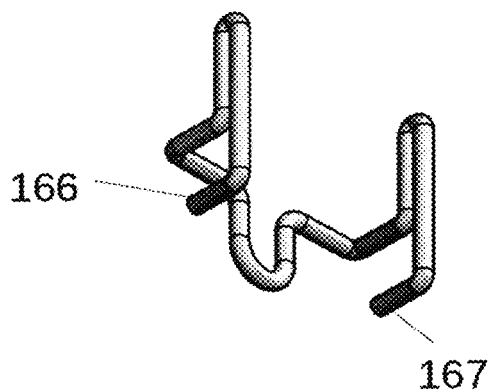
Figure 10B:
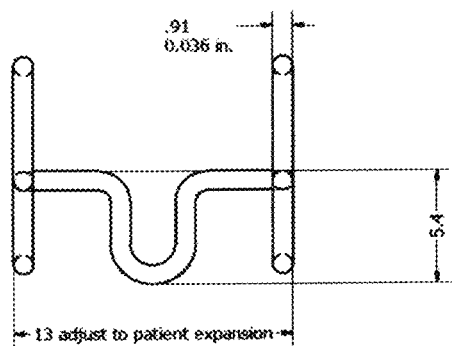
Figure 10C:
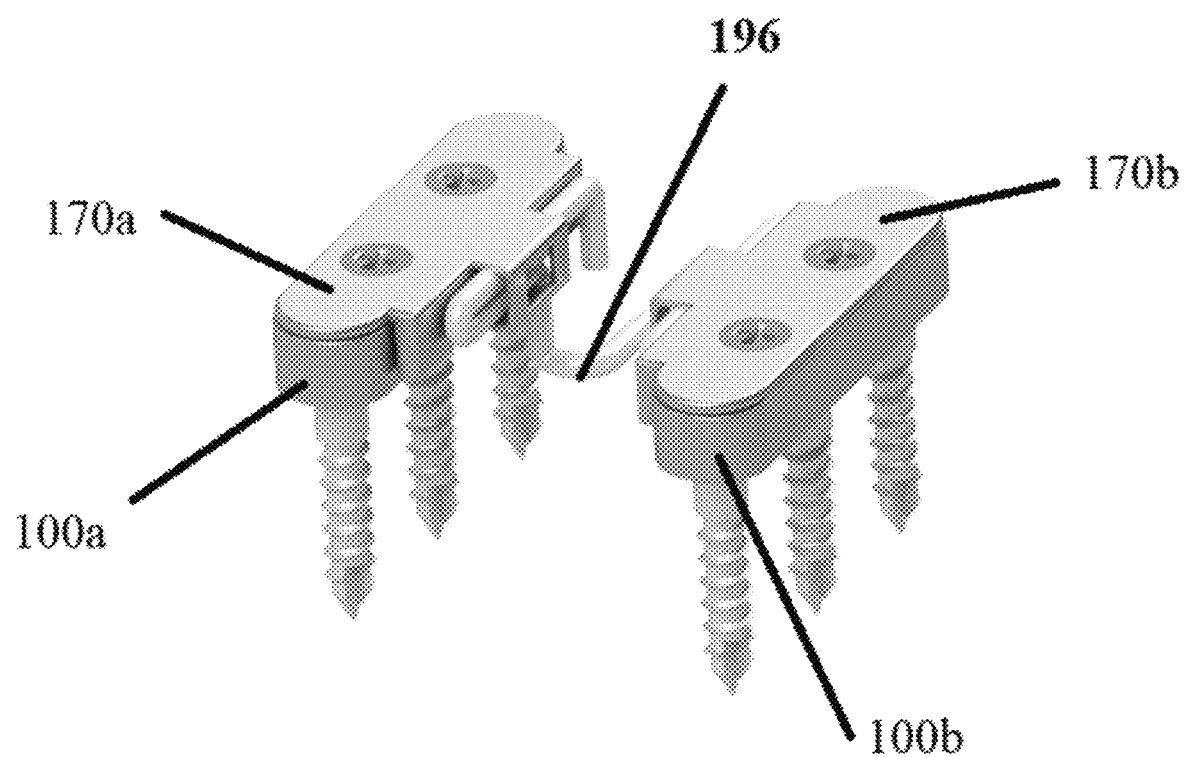
Figure 10D:
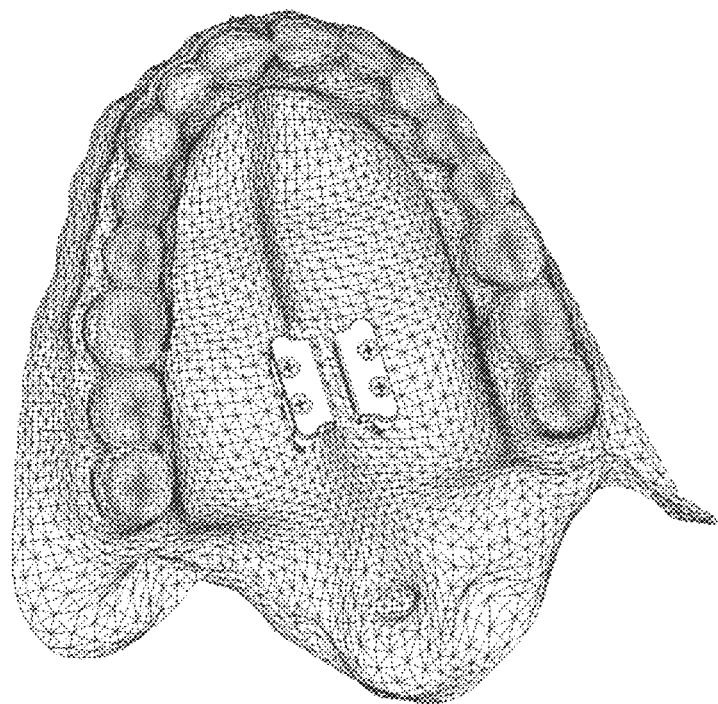

Referring to FIG. 9, there is seen a representation of a pair of first bodies and a pair of third bodies after the pair third bodies are coupled to the pair of first bodies via respective fifth fasteners.

Referring to FIGS. 10a, 10b, 10c, 10d, 10e, 10f and 10a, there are seen representations of components of a skeletal anchorage expander device, including a second fixed aligner.

Figure 11A:
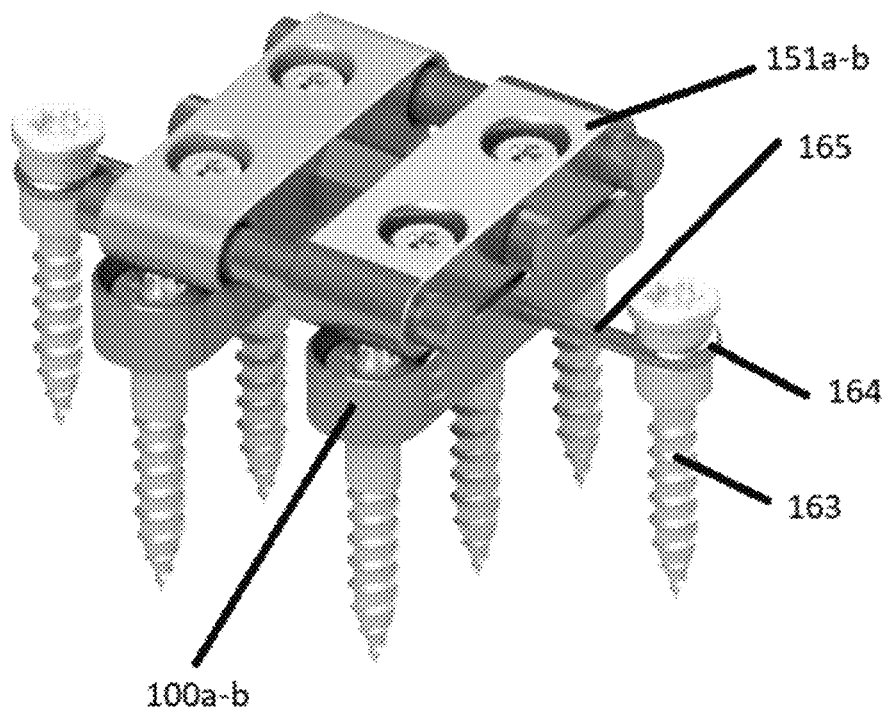
Figure 11B:
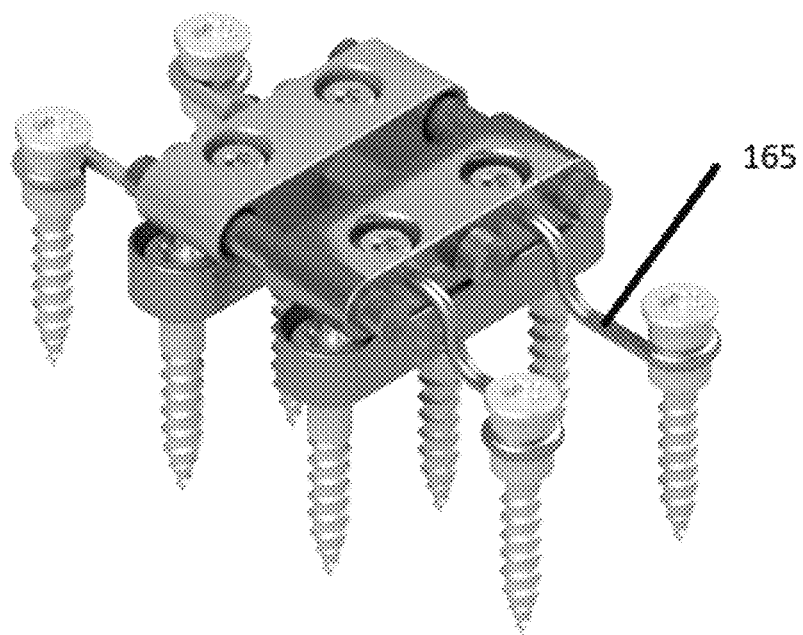

Referring to FIGS. 11a-b there are seen representations of a skeletal anchorage expander device comprised of additional bodies.

Referring to FIGS. 12a-c, there are seen representations of a skeletal anchorage expander device that does not necessarily rely on the use of a pair of first bodies.

Figure 13:
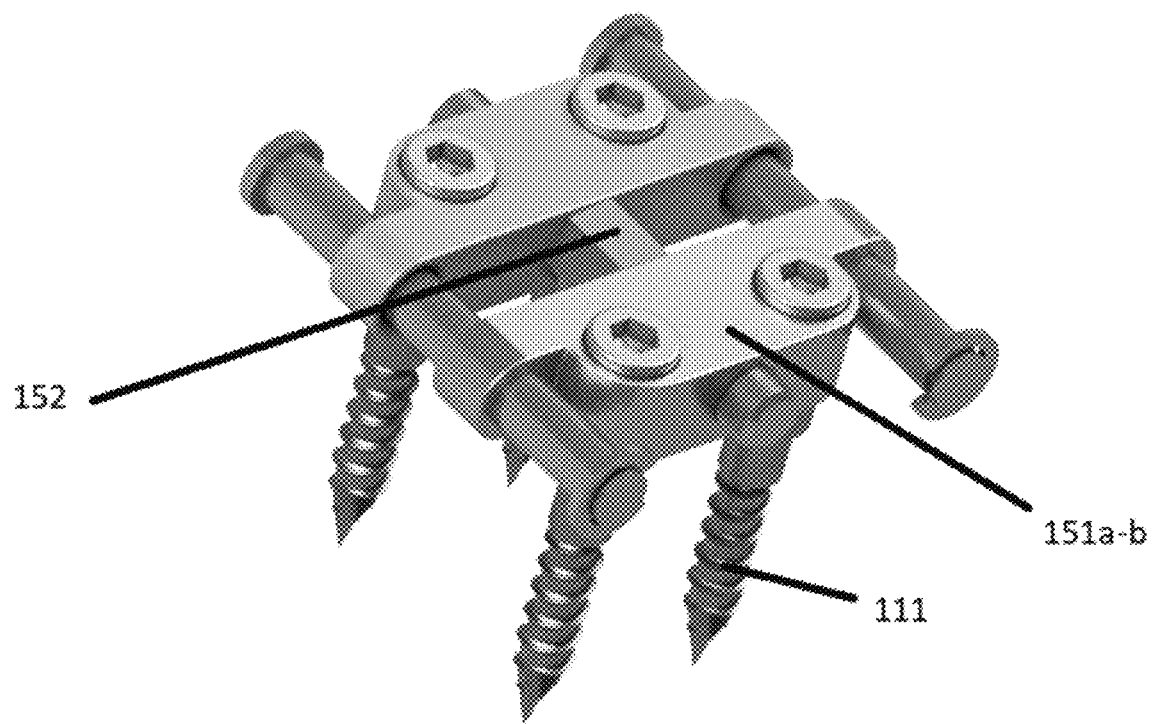

Referring to FIG. 13, there is seen a representation of another embodiment of a skeletal anchorage expander device that does not require use of first bodies 100a-b.

Figure 14:
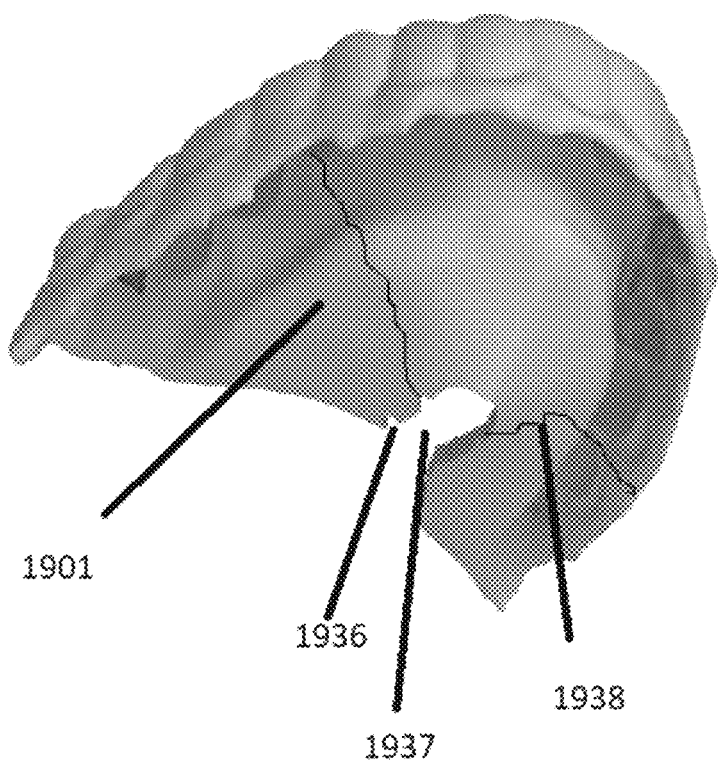

Referring to FIG. 14, there is seen a representation of a third fixed fastener.

SUMMARY

In one embodiment, the present invention comprises a maxillary expander, comprising: a pair of bodies comprised of a first body and a second body, wherein, each of the pair of bodies is configured to be fixed intraorally to a hard palate of a patient; and a fixed aligner, wherein the fixed aligner is configured to be releasably fastened to the pair of bodies to position the pair of bodies a predetermined distance apart. In one embodiment, the present invention comprises a plurality of fasteners; a plurality of apertures formed in the pair of bodies; and a plurality of matching apertures formed in the fixed aligner; the plurality of fasteners configured to fasten the fixed aligner to the pair of bodies via insertion in the plurality of apertures in the pair of bodies and the fixed aligner. In one embodiment, the plurality of apertures comprise four apertures formed in the fixed aligner and two apertures formed in each of the pair of bodies. In one embodiment, a plurality of apertures is formed in each of the pair of bodies; and a plurality of fasteners configured to fasten each of the pair of bodies body to the hard palate via insertion of the plurality of fasteners within the plurality of apertures. In one embodiment, the plurality of apertures in each of the pair of bodies comprises at least three apertures. In one embodiment, the fixed aligner is comprised of two ends, and wherein each of the pair of bodies is configured to be coupled to a respective one of the two ends. In one embodiment, the fixed aligner comprises a wire. In one embodiment, the fixed aligner comprises a curved wire. In one embodiment, the fixed aligner comprises a polymer. In one embodiment, the fixed aligner comprises a spring metal. In one embodiment, the fixed aligner consists of an integral structure. In one embodiment, the fixed aligner consists of a single type of material. In one embodiment, the expander is configured to be fixed to the hard palate with a space present between the pair of bodies and the tissue covering the hard palate. In one embodiment, each of the pair of bodies comprises an elongated plate. In one embodiment, the plurality of apertures in each of the first bodies are disposed along a longitudinal axis of the elongated plate.

In one embodiment, the present invention comprises maxillary expander, comprising: a first pair of bodies, wherein each of the bodies is configured to be coupled to a hard palate; and an adjustable aligner, wherein the adjustable aligner is configured to be releasably fastened to the pair of first bodies to vary a first distance between the first pair of bodies by applying an expansionary force to the first pair of first bodies. In one embodiment, the adjustable aligner comprises a second pair of bodies and an expansion screw disposed between the second pair of first bodies. In one embodiment, the present invention comprises a pair of appliances and at least two supports, wherein each support is comprised of a first end and a second end, wherein first ends of at least two of the supports are each coupled to and extend from a respective one of the pair of first pair of bodies, and wherein second ends of the at least two of the supports are each coupled to the appliances. In one embodiment, the adjustable aligner comprises a pair of appliances each coupled to a respective one of the second pair of first bodies, wherein each of the appliances is configured to match a shape of the hard palate. In one embodiment, the appliances comprise silicone or acrylic. In one embodiment, the appliances are configured to not directly couple to any teeth. In one embodiment, each of the pair of first bodies comprises three apertures configured to receive fasteners. In one embodiment, the three apertures are threaded. In one embodiment, each of the second bodies is configured to be coupled to respective ones of the pair of first bodies by at least two screws.

In one embodiment, the present invention comprises a method of laterally expanding a maxilla of a patient, comprising the steps of: intraorally attaching a pair of first bodies to a hard palate with a first distance between the first bodies; attaching an adjustable aligner to the pair of first bodies; adjusting the adjustable aligner to cause an expansionary force to be applied to the pair of first bodies such that the first distance is changed to a second distance; removing the adjustable aligner from the pair of first bodies; and affixing a first fixed aligner to the pair of first bodies to maintain the second distance between the pair of first bodies. In one embodiment, the step of intraorally attaching the pair of first bodies to the palate comprises affixing a second first fixed aligner to the pair of first bodies to create the first distance; and further comprising a step of de-attaching the first fixed aligner from the pair of first bodies before attaching the adjustable aligner. In one embodiment, the method further comprises a step of affixing an appliance to each of the pair of bodies. In one embodiment, the method further comprises a step of coupling the appliance to the hard palate and not to teeth of the patient. In one embodiment, the step of intraorally attaching the pair of bodies includes attaching one of each of the pair of bodies on either side of a median palatine suture of the patient. In one embodiment, the step of intraorally attaching the pair of bodies includes a step of inserting at least three fasteners through each body and into the hard palate. In one embodiment, the step of inserting comprises threadably coupling each fastener to each body and to the hard palate.

In one embodiment, the present invention comprises a method of expanding a median palatine suture of a patient, comprising the steps of: providing a pair of first bodies; providing a pair of acrylic appliances; intraorally coupling the pair of first bodies and the pair of acrylic appliances to a hard palate of the patient while maintaining a first distance between the pair of first bodies; and applying an expansionary force to the first bodies cause a change the first distance between the first bodies.

In one embodiment, the present invention comprises a method of expanding a maxilla of the patient, comprising the steps of: providing a pair of first bodies; coupling the pair of first bodies to a hard palate of the patient while maintaining a non-zero distance between the pair of first bodies and tissue covering the hard palate of the patient; and attaching an aligner to the pair of first bodies. In one embodiment, the aligner is an adjustable aligner. In one embodiment, the aligner is a fixed aligner. In one embodiment, the distance is between 0.5 to 1.5 mm. In one embodiment, the method further comprises providing a spacer between the pair of first bodies and the hard palate. In one embodiment, the step of coupling comprises use of threaded fasteners. In one embodiment, the distance is maintained via locking of the fastener to the pair of first bodies. In one embodiment, locking comprises a step of gluing, adhering, clamping, screwing, snapping, inserting and/or creating an interference fit.

In one embodiment, the present invention comprises a maxillary expander, comprising: at least two bodies, wherein each of the at least two bodies are configured to be coupled to a hard palate of a patient and to maintain a first distance between the at least two bodies and the hard palate; and an expander configured to maintain a second distance between the at least two bodies. In one embodiment, the expander comprises ends that are threaded. In one embodiment, the expander comprises only one end that is threaded. In one embodiment, the present invention further comprises an aligner. In one embodiment, the aligner comprises at least one body configured to be attached to the at least two of the bodies. In one embodiment, the aligner comprises a fixed aligner. In one embodiment, the aligner comprises an adjustable aligner. In one embodiment, the aligner comprises an expander. In one embodiment, the at least two bodies are configured to receive fasteners. In one embodiment, the fasteners are configured to be received by at least one lateral support extending from each of the at least two bodies. In one embodiment, the fasteners comprise screws. In one embodiment, the fasteners comprise two threaded portions, wherein an outermost diameter of one of the threaded portions is smaller than an outermost diameter of a second of the threaded portions. In one embodiment, the two threaded portions are separated by a non-threaded portion. In one embodiment, the at least two bodies are disposed in a parallel relationship with respect to each other.

In one embodiment, the present invention comprises a method of expanding a maxilla, comprising the steps of: providing at least two bodies; coupling the at least two bodies to a hard palate; and attaching at least one aligner to the at least two bodies. In one embodiment, the at least one aligner comprises a fixed aligner and/or an adjustable aligner. In one embodiment, attaching the at least one aligner comprises attaching a fixed aligner and an adjustable aligner. In one embodiment, the at least two bodies comprise at least one fastener. In one embodiment, the at least one fastener comprises a threaded fastener.

In one embodiment, the present invention comprises a method of applying forces to an upper palate of a patient without engagement of the teeth of the patient, comprising the steps of: providing at least two bodies; coupling the at least two bodies to locations on the upper palate; coupling an adjustable expander to the at least two bodies; and using the adjustable expander to apply a force to the at least two bodies to cause movement of the at least two bodies relative to one another and to cause expansion of the palate. In one embodiment, the adjustable expander comprises threads at opposing ends of the expander. In one embodiment, the movement of the at least two bodies is used to bilaterally expand the maxilla. In one embodiment, the adjustable expander comprises threads at only one end of the expander. In one embodiment, the movement of the at least two bodies is used to unilaterally expand the maxilla. In one embodiment, the locations are on either side of the palatine suture.

In one embodiment, the present invention comprises at least one pair of bodies comprised of a first body and a second body, wherein, each body of the pair of bodies is configured to be coupled intraorally to a palate of a patient; and an aligner, wherein the aligner is coupled to the pair of bodies and configured to position the pair of bodies a distance apart to cause expansion of the palate without any engagement of the aligner or at least one pair of bodies with the teeth of the patient. In one embodiment, the aligner comprises a fixed aligner or an adjustable aligner. In one embodiment, the at least one pair of bodies is selected from the group consisting of two plates, two wires, two fasteners, and two appliances. In one embodiment, each body of the pair of bodies is configured to be coupled intraorally to the hard palate with at least one fastener. In one embodiment, each fastener comprises two parts. In one embodiment, the two parts comprises threaded portions separated by a non-threaded portion. In one embodiment, the two parts are separable. In one embodiment, the two parts are threadably.

DETAILED DESCRIPTION

The figures referenced below refer to components and features of the present invention with reference indicators. Although same components may be shown in different figures, it should be noted that cumulative use of indicators with same components is not used when their use would be superfluous and/or make components more difficult to identify.

Referring to FIGS. 1a-i, there are seen representations of components of a skeletal anchorage device before being coupled intraorally to a patient's upper palate on either side of the median palatine suture.

In one embodiment, a skeletal anchorage expander device of the present invention comprises a pair of first bodies 100a-b (only one body shown in FIGS. 1a, 1d, 1e, and 1f) configured for intra-oral attachment to the upper palate on either side of the median palatine suture. In one embodiment, each body comprises a side configured to face the hard palate and an opposite top side. In one embodiment, one or both sides are flat. In one embodiment, each of the first bodies 100a-b comprises a plurality of first apertures 101 and a plurality of second apertures 102 disposed along a longitudinal axis each first bodies. In one embodiment each first body comprises three first apertures 101 and two second apertures 102. In one embodiment, a skeletal anchorage expander device also comprises a first fixed aligner 106 having a plurality of third apertures 199 configured to receive threaded first fasteners 110. In one embodiment, first fasteners 110 comprise screws configured to be received through the third apertures 199 and threadably screwed into the second apertures 102. In one embodiment, an equal number of third apertures 199 are formed on a lateral first left side of the first fixed aligner 106 as are formed on an opposite lateral right second side. In one embodiment, fixed aligner 106 comprises four third apertures 199. In one embodiment, fixed aligner 106 comprises a single integral body. In one embodiment, first fixed aligner 106 comprises a plate like structure. In one embodiment, the first fixed aligner 106 comprises an H-shaped geometry. In one embodiment, third apertures 199 of the first fixed aligner 106 are configured with a longitudinal spacing "B" that enable them to be coupled to respective second apertures 102 of the pair of first bodies 100a-b with first fasteners 110 inserted in the apertures. In one embodiment, when the pair or first bodies 100a-b are coupled to the first fixed aligner 106 via fasteners, a lateral spacing of the third apertures 199 results in the pair of first bodies 100a-b being separated by a distance "Z". In one embodiment, first fixed aligner 108 and each first body 100a-b are dimensioned with the dimensions noted in FIGS. 1a-i.

In one embodiment of use (see FIG. 1c), a hard palate facing side of first fixed aligner 106 is positioned over respective bodies 100a-b, respective first fasteners 110 are inserted through the third apertures 199 of the first fixed aligner 106, and respective fasteners 110 are screwed into second apertures 102 to couple the first fixed aligner 106 to the pair of first bodies 100a-b. After first fixed aligner 106 and the pair of first bodies 100a-b are coupled, the combination is positioned over a hard palate of a patient such that one of first bodies 100a-b is positioned on one side of the median palatine suture of the patient and the other of first bodies 100a-b is positioned on the other side of the suture.

Referring to FIGS. 2a-f, there are seen representations of components of a skeletal anchorage expander device during their coupling to the hard palate on either side of the median palatine suture.

In one embodiment of use, after the first fixed aligner 106 and the pair of first bodies 100a-b are coupled to each other, they are positioned over the hard palate on either side of the median palatine suture and the combination is coupled to the hard palate via a plurality of threadable second fasteners 111. In one embodiment, each of the first bodies comprises a plurality of threaded first apertures 101 that extend between a hard palate facing side and an opposite side of the pair of first bodies. In one embodiment, each of the pair of first bodies 100a-b comprises three threaded first apertures 101. In one embodiment, threadable second fasteners 111 comprise a bottom portion configured to screw into the hard palate via a set of first threads and a top portion configured to screw into first apertures 101 via a second set of threads. In one embodiment, the first and second set of threads are separated by an unthreaded portion. In one embodiment the first set of threads are defied by an outer diameter that is smaller than an outer diameter of the second set of threads. In one embodiment, second fasteners 111 are dimensioned with the dimensions given in FIGS. 2b-f. In one embodiment of use, bottom portions of second fasteners 111 are inserted through a respective first apertures 101 in the pair of first bodies 100a-b, and after insertion, the bottom portions of the second fasteners 111 are screwably inserted into the hard palate. During insertion of the bottom ends of second fasteners into the hard palate, the top portions of second fasteners 111 are screwed into respective threads of first apertures 101 in the pair of first bodies 100a-b until a surface portion at a top of the second fasteners 111 becomes seated against a surface portion of the first apertures 111. In one embodiment, a torque of 0.1 to 0.2 nm is applied to the second fasteners to cause them to be inserted into cortical bone of the palate and to achieve seating against and in the first bodies. In one embodiment, when second fasteners 111 are seated against and in the first bodies 100a-b, a fixed rigid structure is formed, which rigid structure is made even more rigid via insertion of the second fasteners into the hard palate.

In one embodiment, before insertion of the bottom end of second fasteners 111 into a hard palate, one or more spacer 50 is inserted between a hard palate facing side of the pair of first bodies 100a-b and the hard palate. The one or more spacer is intended to define a distance between the pair of first bodies 100a-b and tissue covering the hard palate. In one embodiment, the distance is 0.5-1.5 mm. In one embodiment of use, second fasteners 111 are screwed into the hard palate until the pair of first bodies 100a-b lightly abut against the one or more spacer 50 and such that the one or more spacer lightly abuts against tissue of the hard palate. In one embodiment, spacer 50 comprises soft silicon. In another embodiment, spacer 50 is made of material that is capable of being dissolved by fluids in the mouth. In one embodiment, spacer 50 comprises a material comprising gluten free wheat, yeast, salt and water that is formed by baking into a thin wafer that is capable dissolving very rapidly when exposed to secretions within the mouth. After insertion of one or more spacer 50 and coupling of a pair of first bodies 100a-b to the hard palate, in one embodiment, the spacer is pulled out or is allowed to dissolve to leave an open space/air gap between the first bodies and the hard palate. In one embodiment, the space/air gap enables that no, or very minimal contact, is made between the first bodies 100a-b and the hard palate, which reduces the potential for tissue necrosis to occur. In doing so, since contact with the hard palate by the first bodies 100a-b is reduced, damage and irritation (necrosis) of the palatal soft tissue is reduced. The present invention should not be limited to formation of a space/gap via that use of the described spacer(s) as other methods can also be used, for example, via temporary anchorage of a pair of first bodies to teeth so as to create the space/gap during insertion of second fasteners 111, where after creation of the space, the temporary anchorage can be removed. Further, while threadable insertion of the top ends of the second fasteners into a pair first bodies is described to rigidly couple second fasteners 111 to the bodies in a position below the palate, the present invention should not be limited to use or threads to achieve such coupling, as in other embodiments biocompatible resins or adhesives; or clamping, locking, and interference fit type coupling mechanisms could be used to couple second fasteners 111 to a pair of first bodies in addition to, or in lieu of, the second set of threads described above.

With reference to FIG. 3, there is seen a representation of components of a skeletal anchorage expander device after a pair of first bodies has been coupled to a palate of a patient and after a first fixed aligner is removed. In one embodiment of use, after second fasteners 111 are coupled to a hard palate of a patient, first fasteners 110 are uncoupled from first bodies 100a-b, and first fixed aligner 106 is uncoupled from the pair of first bodies 100a-b and removed. After removal, it is identified that the pair of first bodies 100a-b will be separated by a distance "D" as was determined by distance "B" of first fixed aligner 106 (see FIG. 1b).

Referring now to FIGS. 4a-e, there are seen a representations of components of a skeletal anchorage expander device that comprises an adjustable aligner and/or a pair of first bodies that are configured to effectuate movement and growth of the maxillary skeletal complex of a patient and the 9 bones that articulate with the maxilla. In one embodiment, a skeletal anchorage expander device of the present invention comprises an adjustable aligner 150 (see FIGS. 4a and 4d). In one embodiment, the adjustable aligner 150 comprises a pair of second bodies 151a-b, where each body is coupled by at least one adjustment mechanism formed therebetween. In one embodiment, each of the second bodies 151a-b is elongated along an axis. In one embodiment, when coupled by an adjustment mechanism 152, each axis is generally parallel to the other axis. In one embodiment, the adjustment mechanism 152 comprises a double ended expansion screw having threads at both of its ends. In one embodiment, the adjustment mechanism 152 is configured to be rotated relative to the pair of second bodies 151a-b so as to cause each of the second bodies to move toward or away from each other via threaded interaction of its ends with threaded apertures in each of the second bodies. In one embodiment, each pair of second bodies 151a-b is configured with apertures dimensioned to slideably receive ends of one or more stabilizing rod 175 thereinto or therethrough. In one embodiment, each of the second bodies 151a-b comprise a plurality of threaded fourth apertures 198 configured to extend between a hard palate facing bottom side and a top side of the second bodies 151a-b. In one embodiment, fourth apertures 198 are longitudinally spaced apart to match the longitudinal spacing between second apertures 102 of each of the pair of first bodies. In one embodiment of use, adjustment mechanism 152 is rotated to a position that enables threadable first fasteners 110 to be aligned to and easily inserted through respective fourth apertures 198 of adjustable aligner 150 and into respective apertures 102 of each of the pair of bodies 100a-b. After being coupled in this manner, the pair of second bodies 151a-b will be spaced apart by the same initial distance "D" as the first bodies 100a-b are spaced apart from each other. After coupling, adjustment mechanism 152 can be used to increase or decrease the lateral distance between the pair of second bodies 151a-b, the pair of first bodies 100a-b and the first fasteners 110, which change in distance can be used to treat a maxillary deficiency of a patient by bi-laterally expanding the maxillary skeletal complex and the 9 bones that articulate with the maxilla. In one embodiment, instead of an adjustment mechanism comprised of a double ended expansion screw 152 having thread at both of its ends as described above, an adjustment mechanism 162 comprises a unilateral expansion screw 162 (see FIG. 4d) where one end of the unilateral expansion screw is threaded and the other is not. In one embodiment, the non-threaded end is inserted into and through an aperture of one of the second bodies 151a-b and left to spin freely within the aperture, while the threaded end is coupled via its threads to a threaded aperture within the other body. The non-threaded end is secured by retainer, for example a circle-clip, at its end to limit longitudinal movement within the aperture relative to the second body. When adjustment mechanism 162 is rotated, one of the second bodies 151a-b remains fixed and the other moves. In one embodiment of use, it is identified that a skeletal anchorage expander device comprised of a unilateral expansion screw as described above can, thus, be used to treat maxillary asymmetry. Although rotation is described above to effect an increase in distance between second bodies 151a-b, it is contemplated that other mechanisms capable of causing movements of the second bodies 151a-b are within the scope of the present invention, for example a spring, a micro-motor, or some other passive or active actuator could be used to effect linear movement between the second bodies. In one embodiment, after coupling of each of the pair of first bodies 100a-b to the hard palate, a total of six fasteners will have been used, three per each first body 100a-b. Compared to use of two second fasteners per first body 100a-b, the present invention's use of three second fasteners per first body enables lessening of forces the fasteners experience during movements of the first bodies as well as lessening of forces experience by local bone supporting the fasteners. Use of more second fasteners 111 distributes the force applied to the fasteners by the resistance by the resistance of the palate to movement generated of the second bodies 151a-b and reduces the force experienced by any one fastener. Accordingly, in other embodiments, as needed or desired, to lessen forces experienced by fasteners and/or local bone supporting the fasteners, more than three second fasteners 111 and more than three apertures in first bodies to receive the fasteners are within the scope of the invention.

Figure 4A:
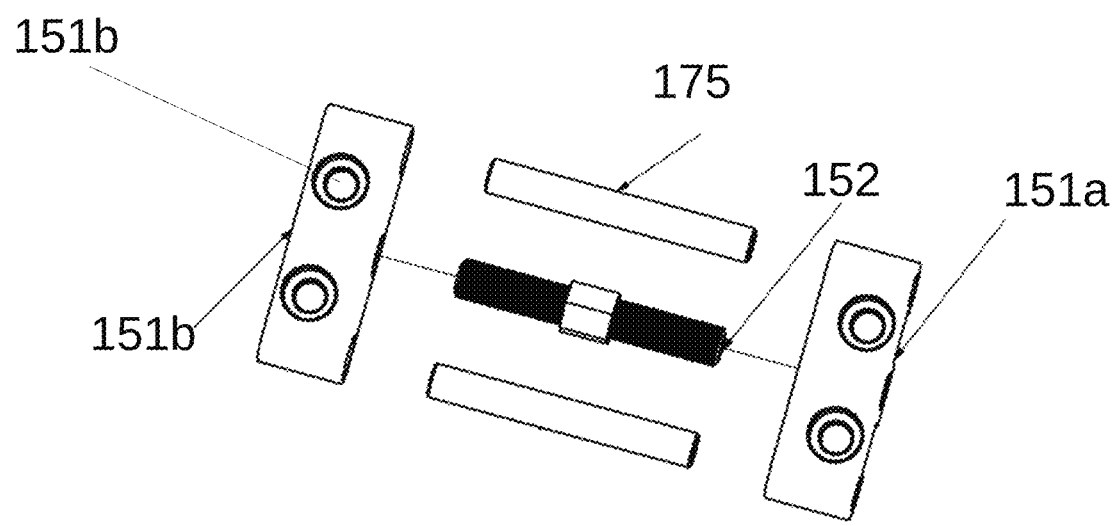
Figure 4B:
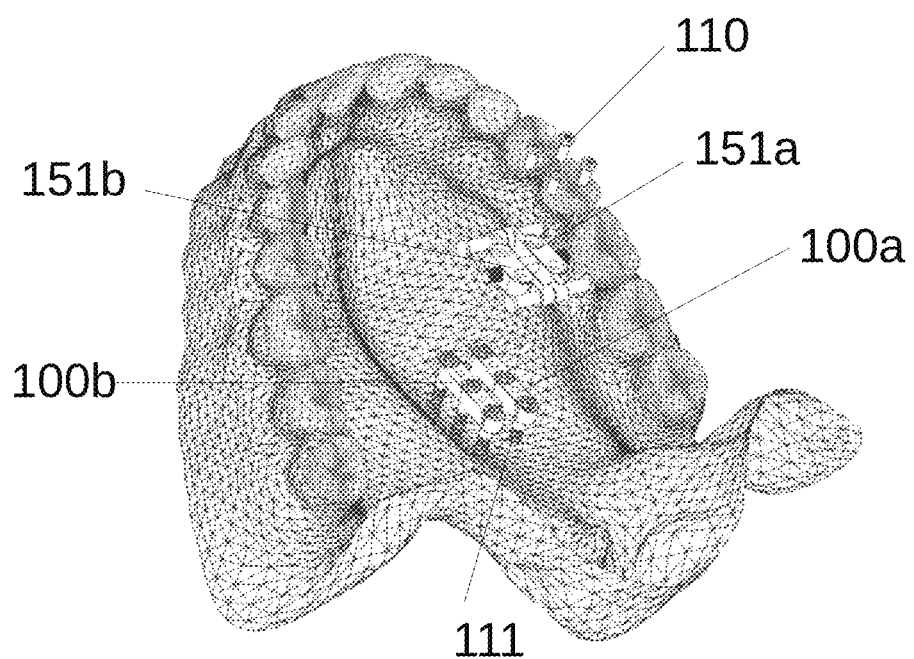
Figure 4C:
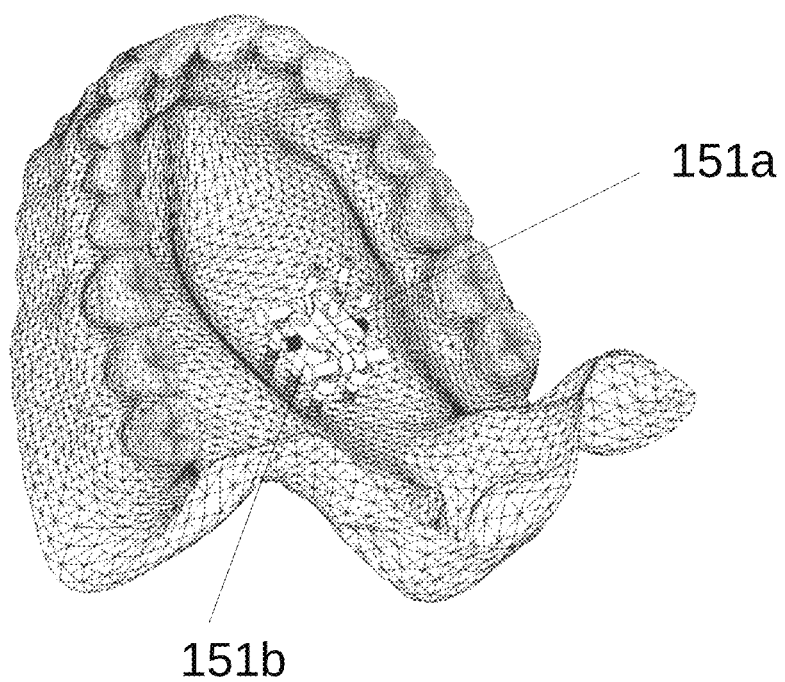
Figure 4D:
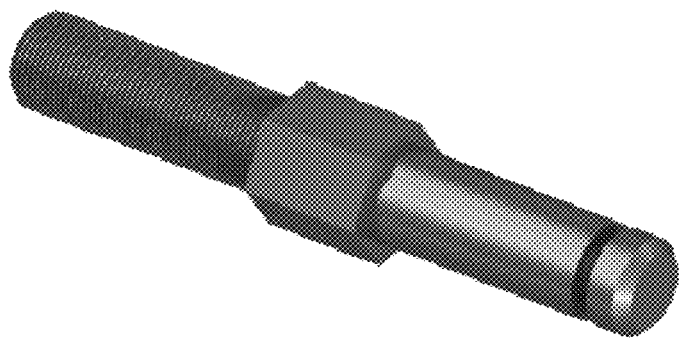
Figure 4E:
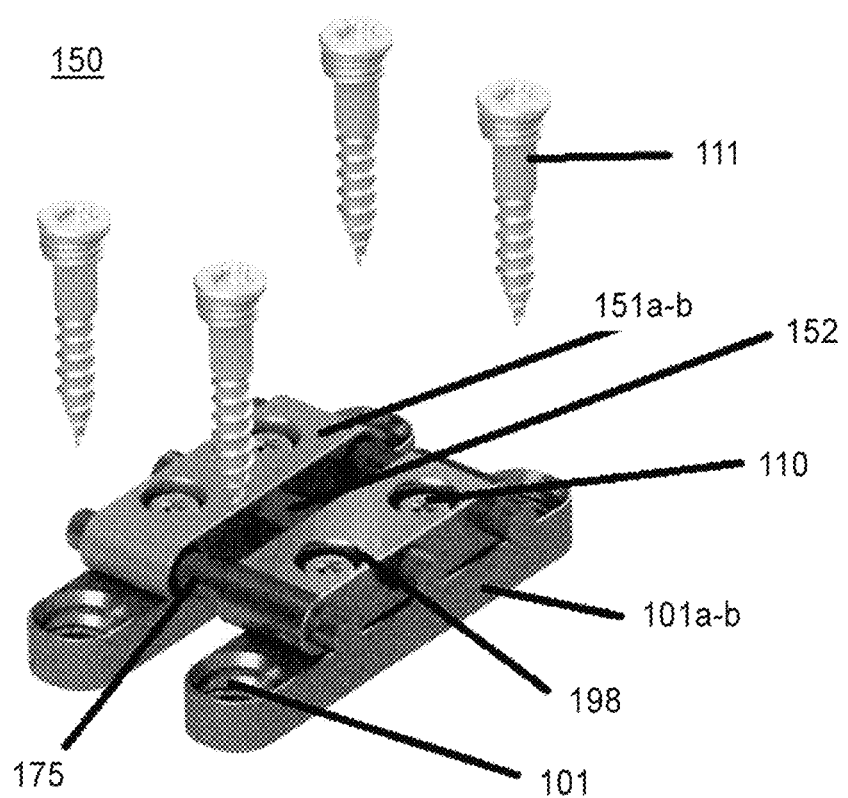

With reference to FIG. 4e, although some embodiments above described use of a fixed aligner 106 to provide initial alignment to a pair of first bodies, in one embodiment, such alignment can be provided without use of aligner 106. In one embodiment of use, threadable first fasteners 110 are inserted through respective fourth apertures 198 of adjustable aligner 150 and then screwed into respective second apertures 102 of a pair of first bodies 100a-b. After being coupled in this manner, the pair of first bodies 100a-b will be spaced apart by an initial distance determined by how much double ended expansion screw 152 will have been rotated. The pair of first bodies 100a-b, can thereafter be coupled to the upper palate with this initial spacing by first inserting four second fasteners 111 into first apertures 101 at both ends of the pair of first bodies 100a-b. After coupling to the upper palate, the adjustable aligner can be removed and as desired two additional second fasteners 111 can be used to secure the pair of first bodies to the hard palate via insertion into first apertures 101 in the middle of the pair of first bodies 100a-b to. Once the pair of first bodies 100a-b is coupled to the upper palate with a full complement of second fasteners 111, adjustable aligner 150 can be coupled to the pair of first bodies 100a-b for use via insertion of threadable first fasteners 110 into fourth apertures 198 of adjustable aligner 150 and then via further insertion into respective second apertures 102 of the pair of first bodies 100a-b.

Figure 5C:
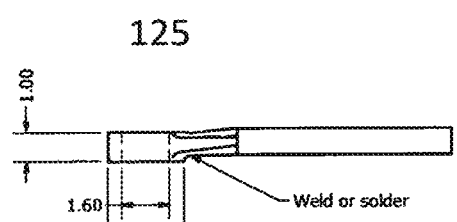
Figure 5B:
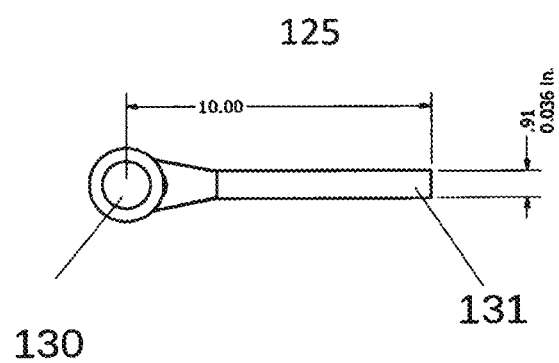

Referring to FIGS. 5a-c, there are seen representations of components a skeletal anchorage expander device, including of a pair of first bodies and a pair of appliances before the appliances are coupled to the pair of first bodies. In some cases, the combination of adjustable aligner 150, first bodies 100a-b, and fasteners 111 may be insufficient to achieve a clinically desired expansion of the maxilla. Accordingly, in one embodiment, a skeletal anchorage expander device of the present invention comprises a pair of appliances 120a-b. In one embodiment each appliance comprises at least one extending support 125 (see FIGS. 5b-c). In one embodiment of use, a first end 130 of each support 125 is configured to be coupled to a respective second aperture 102 of the pair of first bodies 100a-b, and an opposite second end 131 of the supports is embedded within a respective plate 132. In one embodiment, each plate comprises acrylic as is known to be used by those skilled in the dental appliances arts. In one embodiment, when embedded within plate 132, first ends 130 of each extending support 125 are spaced apart by the same distance "Y" as are second apertures 102 of each of the pair of first bodies 100a-b. In one embodiment, each first end 130 comprises an aperture configured to receive a respective fastener 110 therethrough. In one embodiment, plates 132 are made and dimensioned from a mold made of the mouth so that when used intraorally, they comfortably abut against the palatal tissue without any direct contact being made with any teeth.

Figure 6A:
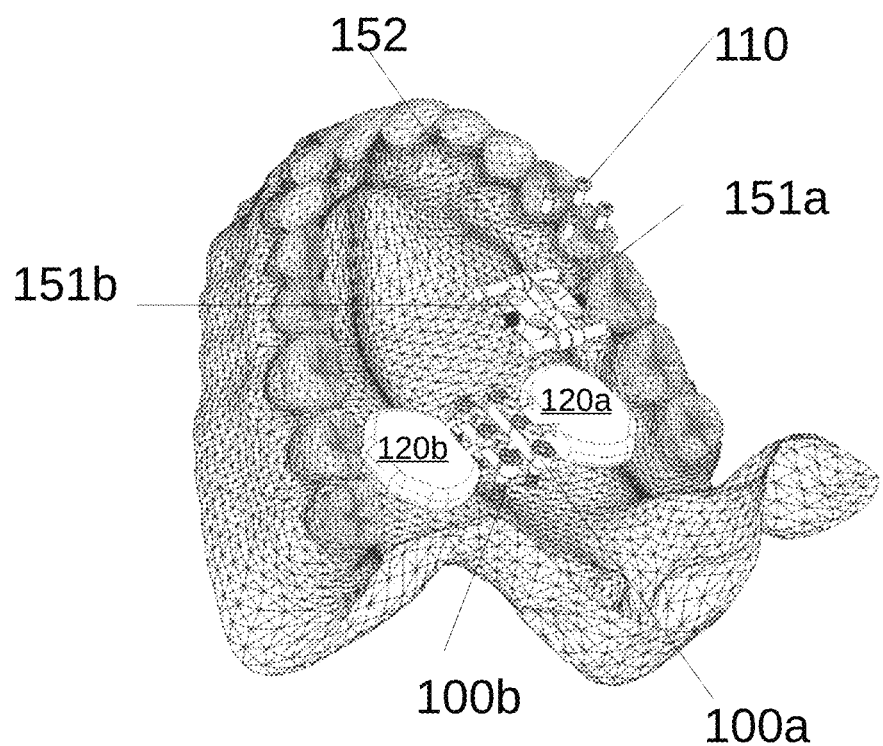
Figure 6B:
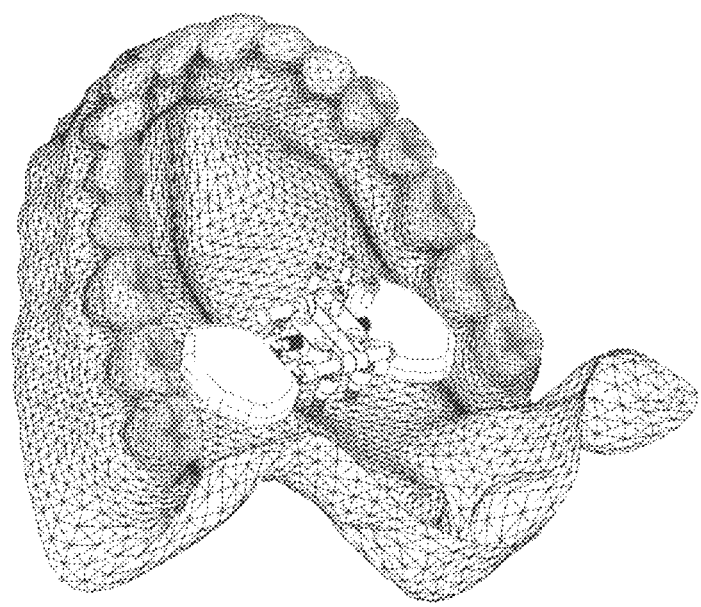
Figure 6C:
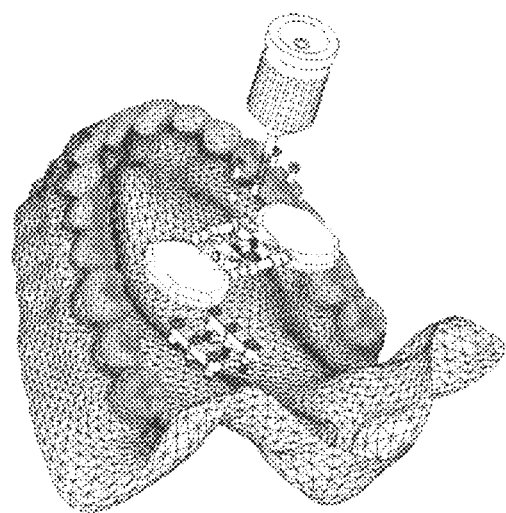
Figure 6D:
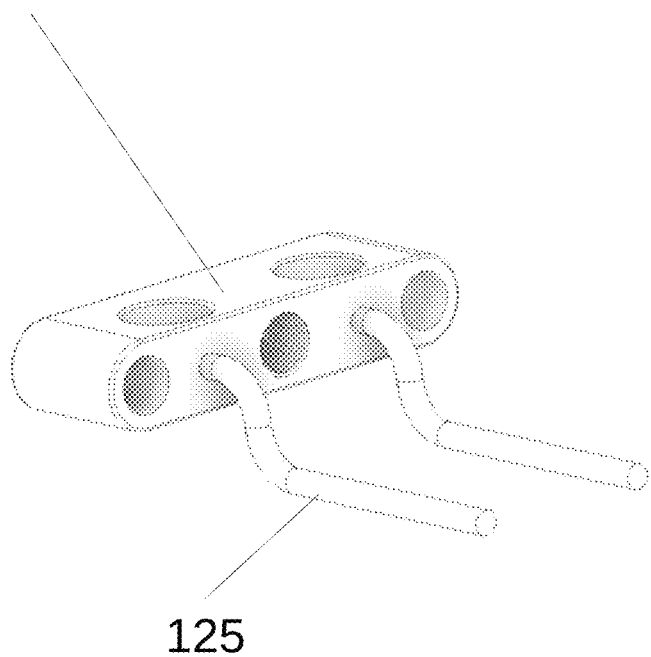

Referring to FIGS. 6a-d, there are seen representations of components of a skeletal anchorage expander device including a pair of appliances coupled to a pair of first bodies before and after an adjustable aligner is coupled to the pair of first bodies and the appliances. In one embodiment of use, threadable first fasteners 110 are inserted through respective fourth apertures 198 of adjustable aligner 150, through respective apertures in first ends 130 of extending supports 125 of appliances 120a-b (see FIGS. 6a-b), and then screwed into respective second apertures 102 of the pair of first bodies 100a-b to cause the three coupled components to form a structure that when coupled to a palate and expanded via adjustment screw 152 enables additional forces to be applied on either side of the palatal suture. In one embodiment (see FIG. 6c), rather than initially provide appliances 120a-b as units separate from that of adjustable aligner 150, each appliance is integrated to be part of respective second body 151a-b, such that the adjustable aligner 150 and each appliance can be attached to the pair of first bodies 100a-b as a single integral unit. FIG. 6d represents one such integration, where a set of first end of supports 125 is integrated into a second body and where the opposite set of ends can be molded over by a plate (not shown).

Referring to FIGS. 7a-b, there are seen representations of components of a skeletal anchorage expander device comprised of appliances before and after a distance between an adjustable aligner is increased by an adjustment mechanism. In one embodiment of use, adjustable aligner 150 is coupled to a pair of first bodies 100a-b and a distance between the pair of second bodies 151a-b is increased via rotation of adjustment mechanism 152, which increase causes a distance between the first bodies 100a-b and appliances 120a-b to be increased. In embodiments, the increase is effected via use of a spanner wrench, activation key, or other device configured to move or rotate adjustment mechanism 152/162. In one embodiment, an incremental increase in a distance between second bodies 151a-b causes lateral expansion of the maxilla of a patient, where the amount of increase is determinative of the amount of potential expansion and that can be achieved. During use of adjustable aligner 150, it is identified that portions of second fasteners 111 at their insertion point into the hard palate are exposed by the small space/gap created between the hard palate and the pair of first bodies 100a-b (see use of spacer 50 to create space/gap in discussion of FIG. 2 above). Compared to if the small space did not exist, the existence of a space causes an increase in the amount of stress the second fasteners are subject too at their insertion point into the hard palate via the aforementioned resistance to movement by the palatine suture at one end of the second fasteners and the movement applied by the second bodies 151a-b at the other end of the fasteners. The stresses applied to the fasteners 111 implies the hard palate at each of the insertion points will also be subject to the stress. A reduction of stress applied to fasteners 111 and the hard palate is thus identified as being desired. One approach to reduce fastener stress includes distributing the stress over more fasteners as discussed above. However, when appliances 120a-b are also used, since their plates 132 abut against the palate, expansion of the second bodies 151a-b will cause the plates to apply forces to the palate, which forces can be used to at least partially overcome the resistance to expansion by the maxilla, which in turn can be used to further reduce stresses experienced by the fasteners. Threadable insertion of the top ends of the second fasteners 111 into respective threaded apertures of the pair of first bodies 100a-b, the use of more than two second fasteners 111 per first body, and the use of appliances as described above can be used alone or in combination to provide stability of the pair of first bodies 100a-b and second bodies 151a-b such that molar and tooth borne anchorage devices do not necessarily need to be used. By eliminating force transmission to the teeth, many benefits are derived, namely, greater orthopedic effects occur relative to alveolar or tooth effects. Greater orthopedic effects are correlated with greater airway and aesthetic benefits. Moreover, many risks are eliminated by the non-involvement and contact with the teeth, including root resorption, tooth tipping, and potentially a scissors bite. Although non-involvement and contact with teeth is preferred, it should be understood that nothing precludes embodiments of the present invention described above or further below from being coupled to the teeth when desired or needed to achieve a particular clinical outcome.

Referring to FIG. 8, there are seen representation of a pair of first bodies after a distance between the adjustable aligner is increased by a clinically desired amount the adjustable aligner and acrylic appliances are removed. In one embodiment of use, after a distance between a pair of first bodies 100a-b is increased to a clinically desired distance "D2", first fasteners 110 are unscrewed, and adjustable aligner 150 and, if used, appliances 120a-b are removed. In one embodiment, to enable regrowth of the palatine suture while distance "D2" is maintained, a pair of third bodies 170a-b are positioned over the pair of first bodies 100a-b. In one embodiment, each of the third bodies 170a-b comprise a plurality of fifth apertures 195 each being longitudinally spaced apart with the same spacing as the second apertures 102 of each first body. In one embodiment, apertures 195 extend from a palatal facing side to a top side of the pair of third bodies 170*a-b* and are configured to receive fifth fasteners 191 therethrough.

Referring to FIG. 9, there are seen representations of a pair of first bodies and a pair of third bodies after the pair third bodies 170*a-b* are coupled to the pair of first bodies via respective fifth fasteners 191 being inserted into respective fifth apertures 195, and the respective fifth fasteners being screwed into respective second apertures 102 of the pair of first bodies 100*a-b* to couple the third bodies to the first bodies.

Referring to FIGS. 10*a-g*, there are seen representations of components of a skeletal anchorage expander device, including a second fixed aligner. In one embodiment of use, to maintain distance "D2" while first bodies 100*a-b* and third bodies 170*a-b* are coupled together, a second fixed aligner 196 is used. In one embodiment second fixed aligner 196 comprises a body configured with a shape that maintains distance "D2" over a holding/stabilizing phase during which a palatine suture of a patient is allowed to regrow with bone and to maintain the distance "D2" on its own and without use of embodiments of the present invention. In one embodiment, second fixed aligner 196 is configured to couple third bodies 170*a-b* together. In one embodiment, second fixed aligner 196 comprises a wire bent into a shape that allows insertion of its ends 166 and 167 into respective sixth apertures 197 formed in each of the pair of third bodies 170*a-b*. In one embodiment, second fixed aligner 196 is manufactured as a single piece from stainless steel spring metal. In one embodiment, second fixed aligner 170*a-b* is manufactured of a material that is sufficiently strong enough to maintain distance 'D2" during the holding/stabilizing phase. Use of fixed aligner 196 during the holding/stabilizing phase instead of an adjustable presents a far sleeker and less bulky apparatus that enables greater tongue volume and tongue posture during the phase. Furthermore, removal of the adjustable aligner after an achieved expansion enables greater hygiene and sanitation.

Referring to FIGS. 11*a-b* there are seen representations of a skeletal anchorage expander device comprised of additional bodies. In some embodiments, during expansion of a patient's maxillary complex, a patient's age, gender, bone density, or a desired clinical outcome may require an amount of stability that some of the embodiments described above are not best suited to provide. Accordingly, in one embodiment, a skeletal anchorage expander is provided with at least two additional bodies 165. In embodiments, bodies 165 comprise extending arms, rods, stiff wires or other structures configured to provide additional points of stability to the skeletal anchorage expander without reliance on support of the teeth. In one embodiment, at least one body extends laterally from each of first bodies 100*a-b* (see FIG. 11*a*) or from each of second bodies 151-*a-b* (see FIG. 11*b*). In one embodiment, one end of each body 165 is integrated with first bodies 100*a-b* or second bodies each body 165, and another end comprises an attachment mechanism 164 configured to provide a coupling to the hard palate. In one embodiment, each attachment mechanism is configured to receive a fastener 163 configured to provide releasable coupling of the attachment mechanism to the hard palate. In embodiments, fastener 163 can comprise screws, rivets, pins, interference type mechanism biocompatible adhesives or other dental fasteners known in the arts. Use of bodies 165 provides additional coupling points via which forces can be distributed across more points of attachment of a skeletal anchorage device to the palate.

Referring to FIGS. 12*a-c*, there are seen representations of a skeletal anchorage expander device that does not necessarily rely on the use of a pair of first bodies. In one embodiment, a skeletal anchorage expander comprises an adjustable aligner 151 or a fixed aligner 106. In one embodiment, a skeletal anchorage expander comprises a plurality of sixth fasteners 136. One bottom end of each sixth fastener 136 is configured to be inserted into the palate and an opposite top end is configured to receive and be coupled to a fixed aligner 106 or an adjustable aligner 150. In one embodiment, a respective alignment and spacing of each sixth fastener 136 relative to other sixth fasteners that are coupled to a patient's hard palate is determined by spacings of apertures formed through fixed aligner 106. In one embodiment, top ends of sixth fasteners 136 are initially coupled to fixed aligner 106 via interference fitment with recesses formed in the bottom of the apertures formed in the fixed aligner 106, where after fitment each sixth fastener extend from and is aligned with the apertures. In one embodiment of use, the fixed aligner 106 and sixth fasteners 136 are aligned to and positioned against the palate so that an equal number of sixth fasteners 136 are positioned on either side of the palatine suture. In one embodiment of use, each fastener is subsequently coupled to the palate. In one embodiment, the bottom end of each sixth fastener 136 comprises threads that are inserted into the palate via rotatable interaction with the top ends of each fastener thorough the apertures in fixed aligner 106. In one embodiment of use, after insertion of each sixth fastener 136 to a desired depth, fixed aligner 106 is decoupled from sixth fasteners 136 via removal of the top ends of the sixth fasteners from the recesses in the apertures of fixed aligner. In one embodiment of use, an adjustable aligner 150 is coupled to the sixth fasteners 136. In one embodiment, attachment mechanisms are provided with or in each second body 151*a-b* and are dimensioned to be longitudinally spaced apart with the same longitudinal spacing as the apertures of fixed aligner 106. In one embodiment, before coupling sixth fasteners 136, the second bodies 151*a-b* are spaced apart using an adjustment mechanism 152 to provide the attachment mechanism in the second bodies 151*a-b* with the same lateral spacing as that of the apertures of fixed aligner 106. In one embodiment, each attachment mechanism in adjustable aligner 150 is configured such that when adjustable aligner 150 is placed over sixth fasteners 136, the attachment mechanism retains adjustable aligner 150. In embodiments, the attachment mechanisms comprise, apertures, snap fit mechanisms, interference type mechanisms, adhesive or combinations thereof that are configured to allow sixth fasteners 135 to be coupled and decoupled to the adjustable aligner 150. In one embodiment, attachment mechanisms comprise apertures and seventh fasteners 135 that are provided in and with each second body 151*a-b*, where seventh fasteners comprise fasteners and where top ends of sixth fasteners 136 are provided with apertures to receive bottom ends of seventh fasteners 135. In one embodiment top ends of sixth fasteners 136 and bottom ends of seventh fasteners 135 are threaded. In one embodiment of use, after adjustable aligner 150 is positioned over sixth fasteners 136, seventh fasteners 135 are inserted into apertures of adjustable aligner and coupled to sixth fasteners 136. Subsequently, adjustable aligner 151 can be used to generate therapeutic expansionary forces to alignably installed sixth fasteners 136, without the need to use first bodies 100 *a-b* described above. Further, in as much as sixth fasteners 135 can be installed into the palate to a desired depth, in one embodiment, installation may be performed such that the top ends of the sixth fasteners 135 can protrude a particular distance below the palate, in which case, one or more spacer 50 as described above may not be needed to achieve a desired mounting space/gap between adjustable aligner 150 and tissue of the palate. Although four sixth 136 and seventh 135 fasteners are represented by FIGS. 12a-b, other numbers of fasteners and attachment mechanism are understood to be capable of implementation and use, for example, six or more sixth and seventh fasteners, and respective six or more attachment mechanisms can used as may be desired or needed to distribute forces experienced by the fasteners.

Referring to FIG. 13, there are seen representations of another embodiment of a skeletal anchorage expander device that does not require use of first bodies 100a-b.

In another embodiment, where a pair of first bodies 100a-b discussed above need not be used, each of the second bodies 151a-b comprise a plurality of threaded fourth apertures 198 that are configured to extend between a hard palate facing bottom side and a top side of the second bodies 151a-b. Although four threaded apertures 198 are discussed herein, the present invention contemplates other numbers of fourth apertures can be implemented within each of the second bodies 151a-b to better distribute forces and decrease screw and bone stress. In one embodiment of use, pair of second bodies 151a-b are first coupled to the upper palate by inserting bottom ends second fasteners 111 into fourth apertures 198, and after insertion the bottom ends of the second fasteners 111 are screwably inserted into the hard palate. During insertion of the bottom end into the hard palate, the top end of second fasteners 111 are screwed into respective threaded fourth apertures 101 in the pair of second bodies 151a-b. In one embodiment, before full screwable insertion of the second fasteners 111 into the palate, a spacer 50 may be used to create a distance between the pair of second bodies 151a-b and the palate. In one embodiment, when used without the pair of first bodies as described above, the pair of second bodies 151a-b can be coupled to or comprise an acrylic appliance, arm, rod, stiff wire or other structure configured to provide additional points of stability to the skeletal anchorage expander as described above.

Referring to FIG. 14, there is seen a representation of a third fixed fastener. In one embodiment, a third fixed aligner 1901 comprises a surgical guide that is configured to centrally position and fixate a pair of first bodies 100a-b (not shown in FIG. 14—see FIG. 1a) within a recess 1937 and such that the first bodies can be positioned against the palate a predetermined distance apart. In one embodiment, a cast or computer scan of a patient' upper jaw is obtained from which the third fixed fastener is made such that anatomical features of the palate are embossed in third fixed aligner 1901 for use as a guide that can be used mount first bodies with recess 1937 and against the patient's palate. In one embodiment, third fixed aligner 1901 is configured to guide first bodies 100a-b into a position on either side of a palatine suture. In one embodiment, once a mounting location for first bodies 100a-b on the third fixed aligner 1901 is determined, one or more apertures 1936 can be formed in the third fixed aligner 1901 to guide insertion of second fasteners 111 into the hard palate. In one embodiment, apertures 1936 are formed along recess 1937 formed in the third fixed aligner. In one embodiment of use, third fixed aligner 1901 is positioned in the patient's mouth in a manner that features of the surgical guide fit against matching features of the hard palate, after which, first bodies 100a and second fasteners 111 protruding through apertures in the pair of first bodies 100a-b can be coupled to the hard palate via insertion of the fasteners into apertures 1936. Next, fasteners 111 can be rotated into the hard palate until threads at their top become fixed in and against the pair of first bodies. In one embodiment, third fixed aligner 1901 is made from a relatively rigid, but frangible material, for example, biocompatible acrylic or polycarbonate. In one embodiment, third fixed aligner 1901 is provided with one or more thinned region 1938 to enable removal of the fixed aligner via subsequent breakage. In one embodiment, subsequent to fixation of second fasteners 111 in the pair of first bodies 100a-b and the hard palate, the third fixed aligner 1901 is removed, for example, via selective removal from around the fasteners and under the pair of first bodies 100a-b. When inserted into a patient's mouth and first bodies 100a-b are coupled to the third fixed aligner 1901 and the patient's palate, the third fixed aligner defines a space/gap between the first bodies 100a-b similar to that provided by spacer 50 described above. Accordingly, in embodiments, third fixed aligner 1901 is manufactured with different thicknesses in the area around apertures 1936 according to a particular space/or gap desired, for example, 0.5 to 1.5 mm.

Comparison of Prior art against various embodiments of the present invention were performed, including for:

Prior Art: an expander assembly coupled to the teeth via molar bands and to the palate via 4 fasteners comprised of only one set of threads that are inserted into the palate (i.e. Moon device referenced in Background)

Embodiment 1: An expander assembly using an adjustable aligner 150 coupled to the palate via a pair of first bodies 100a-b and six fasteners 111, where each fastener comprises two sets of threads (see FIG. 2b).

Embodiment 2: An expander assembly using an adjustable aligner 150 coupled to the palate via a set of two bodies 120a-b (see FIG. 6b) and a pair of first bodies 100a-b and six fasteners 111, where each fastener comprises two sets of threads (see FIG. 2b)

The following peak bone stresses were noted:

Prior Art: 98 MPa

Embodiment 1: 84 MPa (provided reduced stresses to fasteners and bone compared to prior art).

Embodiment 2: 50 MPa (provided reduced stresses to fasteners and bone compared to prior art).

The peak palatine strains for the four assemblies were noted:

Prior Art: 0.479

Embodiment 1: 0.426 (provided more uniform strain to the palatine suture compared to prior art).

Embodiment 2: 0.397 (provided more uniform strain to the palatine suture compared to prior art).

The preceding embodiments have been described in some detail to facilitate understanding, the described embodiments are to be considered illustrative and not limiting. It will be apparent to one of ordinary skill in the art that certain changes and modifications can be practiced within the scope of the appended claims.

For example, one or more features from any embodiment may be combined with one or more features of any other embodiment without departing from the scope of the disclosure. Further, modifications, additions, or omissions may be made to any embodiment without departing from the scope of the disclosure. Additionally other dimensions and other materials other than those disclosed can be used as long as they are compatible as well as sufficiently robust for human use.

What is claimed:

1. A method of applying forces to a maxilla of a patient, comprising:
   providing at least two bodies, wherein each of the at least two bodies comprises three first apertures configured to receive fasteners;
   coupling the at least two bodies to locations on the maxilla, wherein the locations are on either side of a palatine suture;
   coupling an adjustable expander to the at least two bodies, after the at least two bodies are coupled to the maxilla;
   using the adjustable expander to apply a force to the at least two bodies, after the adjustable expander is coupled to the at least two bodies, to cause movement of the at least two bodies relative to one another and to cause expansion of the maxilla.

2. The method of claim 1, wherein the adjustable expander comprises a second pair of bodies and an expansion screw disposed between the second pair of bodies.

3. The method of claim 1, wherein the adjustable expander comprises a pair of appliances each coupled to a different one of the at least two bodies, wherein each of the appliances is configured to match a shape of the maxilla.

4. The method of claim 3, wherein the appliances comprise silicone or acrylic.

5. The method of claim 3, wherein the appliances are configured to not directly couple to any teeth.

6. The method of claim 2, wherein each of the second pair of bodies is configured to be coupled to a different one of the at least two bodies by at least two screws.

7. The method of claim 2, wherein the expansion screw comprises threads at opposing ends.

8. The method of claim 7, wherein the movement of the at least two bodies is used to bilaterally expand the maxilla.

9. The method of claim 2, wherein the expansion screw comprises threads at only one end.

10. The method of claim 9, wherein the movement of the at least two bodies is used to unilaterally expand the maxilla.

11. The method of claim 1, wherein the at least two bodies each comprise threaded first apertures.

12. The method of claim 11, wherein:
   the at least two bodies are coupled to the maxilla with fasteners, and
   the fasteners each comprise (i) a bottom portion comprising first threads configured to screw into the maxilla, and (ii) a top portion comprising second threads configured to screw into the threaded first apertures.

13. The method of claim 12, wherein each of the at least two bodies is coupled to the maxilla with a plurality of fasteners.

14. The method of claim 1, wherein the method does not comprise applying force on any of the teeth of the patient.

15. The method of claim 1, wherein each of the at least two bodies comprises second apertures configured to receive screws, and
   the second apertures do not pass through the at least two bodies.

16. The method of claim 12, wherein each of the at least two bodies comprises second apertures configured to receive screws, and
   the second apertures do not pass through the at least two bodies.

17. A method of applying forces to a maxilla of a patient, comprising:
   providing at least two bodies;
   coupling the at least two bodies to locations on the maxilla, wherein the locations are on either side of a palatine suture; followed by
   coupling an adjustable expander to the at least two bodies; followed by
   using the adjustable expander to apply a force to the at least two bodies to cause movement of the at least two bodies relative to one another and to cause expansion of the maxilla, and
   further comprising, subsequent to the coupling of the adjustable expander to the at least two bodies, uncoupling the adjustable expander from the at least two bodies; followed by
   coupling a fixed aligner to the at least two bodies.

18. The method of claim 17, wherein the at least two bodies each comprise threaded first apertures.

19. The method of claim 18, wherein:
   the at least two bodies are coupled to the maxilla with fasteners, and
   the fasteners each comprise (i) a bottom portion comprising first threads configured to screw into the maxilla, and (ii) a top portion comprising second threads configured to screw into the threaded first apertures.

20. The method of claim 19, wherein each of the at least two bodies is coupled to the maxilla with a plurality of fasteners.

21. The method of claim 19, wherein each of the at least two bodies comprises second apertures configured to receive screws, and
   the second apertures do not pass through the at least two bodies.

22. A method of applying forces to a maxilla of a patient, comprising:
   providing at least two bodies, and an aligner coupled to the at least two bodies;
   coupling the at least two bodies to locations on the maxilla, wherein the locations are on either side of a palatine suture;
   uncoupling the aligner from the at least two bodies, after the at least two bodies are coupled to the maxilla;
   coupling an adjustable expander to the at least two bodies, after uncoupling the aligner from the at least two bodies; and
   using the adjustable expander to apply a force to the at least two bodies, after the adjustable expander is coupled to the at least two bodies, to cause movement of the at least two bodies relative to one another and to cause expansion of the maxilla.

23. The method of claim 22, wherein the at least two bodies each comprise threaded first apertures.

24. The method of claim 23, wherein:
   the at least two bodies are coupled to the maxilla with fasteners, and
   the fasteners each comprise (i) a bottom portion comprising first threads configured to screw into the maxilla, and (ii) a top portion comprising second threads configured to screw into the threaded first apertures.

25. The method of claim 24, wherein each of the at least two bodies is coupled to the maxilla with a plurality of fasteners.

26. The method of claim 24, wherein each of the at least two bodies comprises second apertures configured to receive screws, and
   the second apertures do not pass through the at least two bodies.

27. The method of claim 22, wherein each of the at least two bodies is coupled to the maxilla with a plurality of fasteners.

28. The method of claim 22, wherein the adjustable expander comprises a second pair of bodies and an expansion screw disposed between the second pair of bodies.

29. The method of claim 28, wherein each of the second pair of bodies is configured to be coupled to a different one of the at least two bodies by at least two screws.

30. A method of applying forces to a maxilla of a patient, comprising:
   providing at least two bodies, and an aligner coupled to the at least two bodies, wherein each of the at least two bodies comprises at least three threaded first apertures;
   coupling with fasteners the at least two bodies to locations on the maxilla with a space present between the at least two bodies and tissue covering the maxilla, wherein the locations are on either side of a palatine suture, and the fasteners each comprise (i) a bottom portion comprising first threads configured to screw into the maxilla, and (ii) a top portion comprising second threads configured to screw into each of the at least three threaded first apertures;
   uncoupling the aligner from the at least two bodies, after the at least two bodies are coupled to the maxilla;
   coupling an adjustable expander to the at least two bodies, after uncoupling the aligner from the at least two bodies; and
   using the adjustable expander to apply a force to the at least two bodies, after the adjustable expander is coupled to the at least two bodies, to cause movement of the at least two bodies relative to one another and to cause expansion of the maxilla.

31. The method of claim 30, further comprising, subsequent to the coupling of the adjustable expander to the at least two bodies, uncoupling the adjustable expander from the at least two bodies; followed by
   coupling a fixed aligner to the at least two bodies.

32. The method of claim 30, wherein each of the at least two bodies comprises second apertures configured to receive screws, and
   the second apertures do not pass through the at least two bodies.

* * * * *